US007153515B2

(12) United States Patent
Brown et al.

(10) Patent No.: US 7,153,515 B2
(45) Date of Patent: Dec. 26, 2006

(54) METHOD OF PREVENTING T CELL-MEDIATED RESPONSES BY THE USE OF THE MAJOR HISTOCOMPATIBILITY COMPLEX CLASS II ANALOG PROTEIN (MAP PROTEIN) FROM *STAPHYLOCOCCUS AUREUS*

(75) Inventors: Eric Brown, Houson, TX (US); Lawrence Lee, Houston, TX (US); Magnus Hook, Houston, TX (US)

(73) Assignee: The Texas A&M University System, College Station, TX (US)

( * ) Notice: Subject to any disclaimer, the term of this patent is extended or adjusted under 35 U.S.C. 154(b) by 310 days.

(21) Appl. No.: 10/041,775

(22) Filed: Jan. 10, 2002

(65) Prior Publication Data

US 2003/0108564 A1 Jun. 12, 2003

Related U.S. Application Data

(60) Provisional application No. 60/260,523, filed on Jan. 10, 2001.

(51) Int. Cl.
*A61K 39/085* (2006.01)
*A61K 39/02* (2006.01)
*A61K 45/00* (2006.01)
*A61K 38/00* (2006.01)

(52) U.S. Cl. ............................... 424/243.1; 424/234.1; 424/190.1; 424/282.1; 424/237.1; 514/2

(58) Field of Classification Search ............ 424/234.1, 424/237.1, 190.1, 282.1, 243.1; 514/862, 514/2, 921; 530/350, 825
See application file for complete search history.

(56) References Cited

U.S. PATENT DOCUMENTS 5,648,240 A 7/1997 Hook et al. ................ 435/69.3
6,222,021 B1 * 4/2001 Wainwright et al. ........ 530/395
2002/0028211 A1 * 3/2002 Kaempfer et al. ....... 424/190.1

FOREIGN PATENT DOCUMENTS

WO WO-02/34788 5/2002
WO WO-02/094868 11/2002

OTHER PUBLICATIONS

Jonsson et al., "*Staphylococcus aureus* Expresses a Major Histocompatibility Complex Class II Analog", The Journal of Biological Chemistry, vol. 270, No. 37, Sep. 15, 1995, pp. 21457-21460.

McGavin et al., "Identification of a *Staphylococcus aureus* Extracellular Matrix-Binding Protein with Broad Specificity", Infection and Immunity, Jun. 1993, vol. 61, No. 6, pp. 2479-2485.

* cited by examiner

*Primary Examiner*—S. Devi
(74) *Attorney, Agent, or Firm*—B. Aaron Schulman; Stites & Harbison PLLC

(57) ABSTRACT

A method of immunomodulating the T cell response in Staphylococcal bacteria is provided wherein an effective amount of the Map protein from *Staphylococcus aureus* is administered to a host to prevent or suppress the T cell response. The present method may be utilized with either the Map protein or an effective subdomain or fragment thereof such as the Map 10 or Map 19 protein. The present invention is advantageous in that suppression or prevention of the T cell response in a host can prevent or ameliorate a wide variety of the pathogenic conditions such as T cell lymphoproliferative disease and toxic shock syndrome wherein the overstimulation of T cells needs to be suppressed or modulated.

4 Claims, 7 Drawing Sheets

METHOD OF PREVENTING T CELL-MEDIATED RESPONSES BY THE USE OF THE MAJOR HISTOCOMPATIBILITY COMPLEX CLASS II ANALOG PROTEIN (MAP PROTEIN) FROM *STAPHYLOCOCCUS AUREUS*

CROSS-REFERENCE TO RELATED APPLICATIONS

This application claims the benefit of U.S. Provisional application Ser. No. 60/260,523, filed Jan. 10, 2001.

FIELD OF THE INVENTION

The present invention relates in general to the utilization of major histocompatibility complex class II analog protein, or "Map" protein, and its biologically effective fragments and domains thereof, in therapeutic methods to combat conditions associated with T cell proliferation, and in particular to the use of the Map protein and effective or active fragments thereof, including the Map10 or Map19 protein, in methods of suppressing or modulating T cell-mediated responses where necessary to alleviate a pathogenic condition.

BACKGROUND OF THE INVENTION

*Staphylococcus aureus* (SA) is an opportunistic pathogen that can cause a wide spectrum of infections from superficial local skin infections to life-threatening systemic infections that can affect internal organs and tissues. In addition, bacterial arthritis, as well as acute and chronic osteomyelitis caused by haematogenous spread or by direct inoculation in open trauma or surgical intervention such as internal fixation or joint replacement, affect hundreds of thousands of patients each year (1–6). SA is also a major cause of infections associated with indwelling medical devices, such as catheters and prosthesis (6). The cost to society in patient care, which often involves extended hospital stays and repeated surgery, can be estimated at several billion dollars per year. With the documented emergence of multidrug resistance SA strains, the threat of this widely distributed pathogen is now appreciated and novel therapies for treatment and prevention are needed.

The successful colonization of the host is a process required for most microorganisms, including *S. aureus,* to cause infections in animals and humans. Microbial adhesion is the first crucial step in a series of events that can eventually lead to disease. Pathogenic microorganisms colonize the host by attaching to host tissues or serum conditioned implanted biomaterials, such as catheters, artificial joints, and vascular grafts, through specific adhesins present on the surface of the bacteria. MSCRAMM™S (Microbial Surface Components Recognizing Adhesive Matrix Molecules) are a family of cell surface adhesins that recognize and specifically bind to distinct components in the host's extracellular matrix. Once the bacteria have successfully adhered and colonized host tissues, their physiology is dramatically altered and damaging components such as toxins and proteolytic enzymes are secreted. Moreover, adherent bacteria often produce a biofilm and quickly become more resistant to the killing effect of most antibiotics.

*S. aureus* is thus known to express a repertoire of different MSCRAMM™S that can act individually or in concert to facilitate microbial adhesion to specific host tissue components. A search for such MCSRAMM's which recognized host components uncovered a 72-kDa protein identified as the major histocompatibility complex class II analog protein, or "Map" protein, a surface localized protein expressed by virtually every *S. aureus* strain (7). Cloning and sequencing of the gene encoding the Map protein revealed a protein consisting of roughly 110-amino acid-long domains repeated six times with each domain containing a 31 amino acid-long subdomain with homology to MHC Class II. If conservative amino acid substitutions were included, the respective subdomains were 61, 65, 52, 59, 52 and 45% similar to the amino-terminal end of the b chain of many MHC class II proteins from different mammalian species (8).

However, previous studies varied with regard to how the Map protein affected immune function, and thus it would be highly desirable to utilize the Map protein so as to affect the T cell immune responses in cases where pathogenic conditions result from a proliferation of T cells.

SUMMARY OF THE INVENTION

Accordingly, it is an object of the present invention to provide a method of utilizing the *S. aureus* Map protein, or effective fragments and domains thereof, to suppress or modulate the T cell response in human or animal patients.

It is also an object of the present invention to provide and utilize binding subdomains of the *S. aureus* MAP protein, including the Map19 protein, in methods of treating or protecting against conditions associated with the overstimulation of T cells.

It is also an object of the present invention to provide isolated Map proteins and active fragments and regions therefrom to prevent T cell-mediated responses in human or animal patients thus reduce or prevent pathogenic and deleterious conditions that arise because of T cell proliferation.

These and other objects are provided by virtue of the present invention which provides methods of utilizing the Map protein and/or its binding subdomains or other effective fragments thereof, to suppress or modulate the T cell immune response in human or animal patients under circumstances where such a response has deleterious consequences. Use and administration of an effective amount of the Map protein or its effective subdomains or fragments thereof can thus be utilized in a host to reduce T cell proliferation and achieve a significant reduction in T cell-mediated processes such as delayed-type hypersensitivity (DTH). Suitable compositions and vaccines based on the isolated MAP protein and its effective regions and subdomains, such as the Map10 and Map19 proteins, as well as methods for their use, are also contemplated by the present invention.

These embodiments and other alternatives and modifications within the spirit and scope of the disclosed invention will become readily apparent to those skilled in the art from reading the present specification and/or the references cited herein, all of which are incorporated by reference.

BRIEF DESCRIPTION OF THE DRAWING FIGURES

FIGS. 1*a*–1*c* are graphic representations showing the Map-induced inhibition of DTH in accordance with the present invention. DpbA-immunized mice were treated with either native Map (A) or recombinant Map19 (B-C) on the day of immunization (day 0) and on days 2, 4, and 6 post immunization. On day 7, BALB/c (A-B) and C3H/Hen (C) mice were challenged with DbpA and footpads were measured 0 and 24 h after challenge. Mice treated with supernatant from Map$^+$SA (A) or recombinant Map19 (B-C) had a significantly reduced DTH response compared to immunized and challenged mice ($p<0.0001$*; Student's t test). Data are expressed as the mean±SE of 5 mice.

Figure 2:
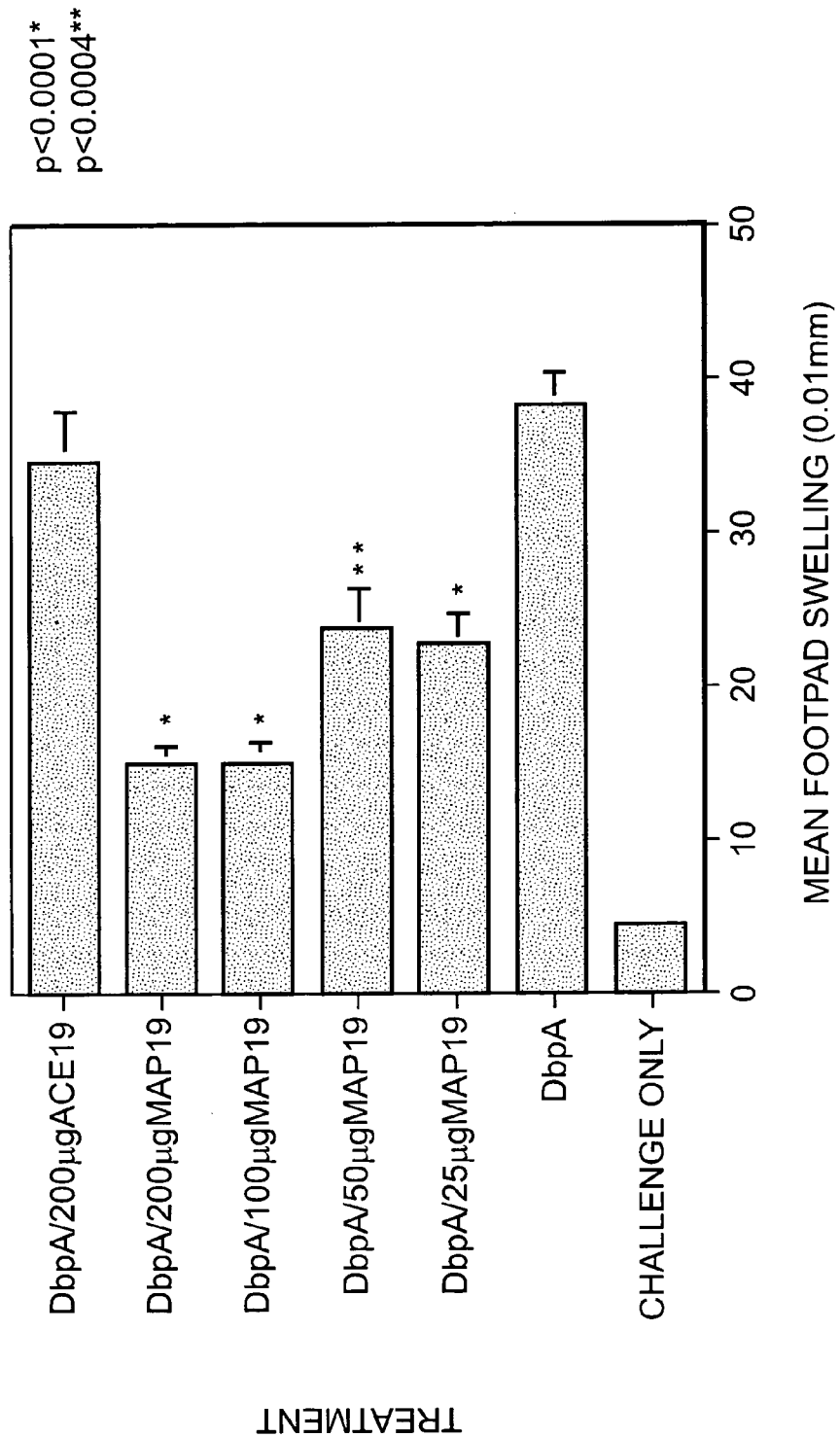

FIG. 2 shows the Map19 dose-response for inhibition of DTH in accordance with the present invention. DbpA-immunized mice were treated with various doses of Map19 (25–200 μg) or ACE19 (200 μg) as described previously. On day 7, mice were challenged with DbpA and footpads were measured 0 and 24 h after challenge. Significant values are indicated by an * (Students t test). Data are expressed as the mean±SE of 5 mice.

Figure 3:
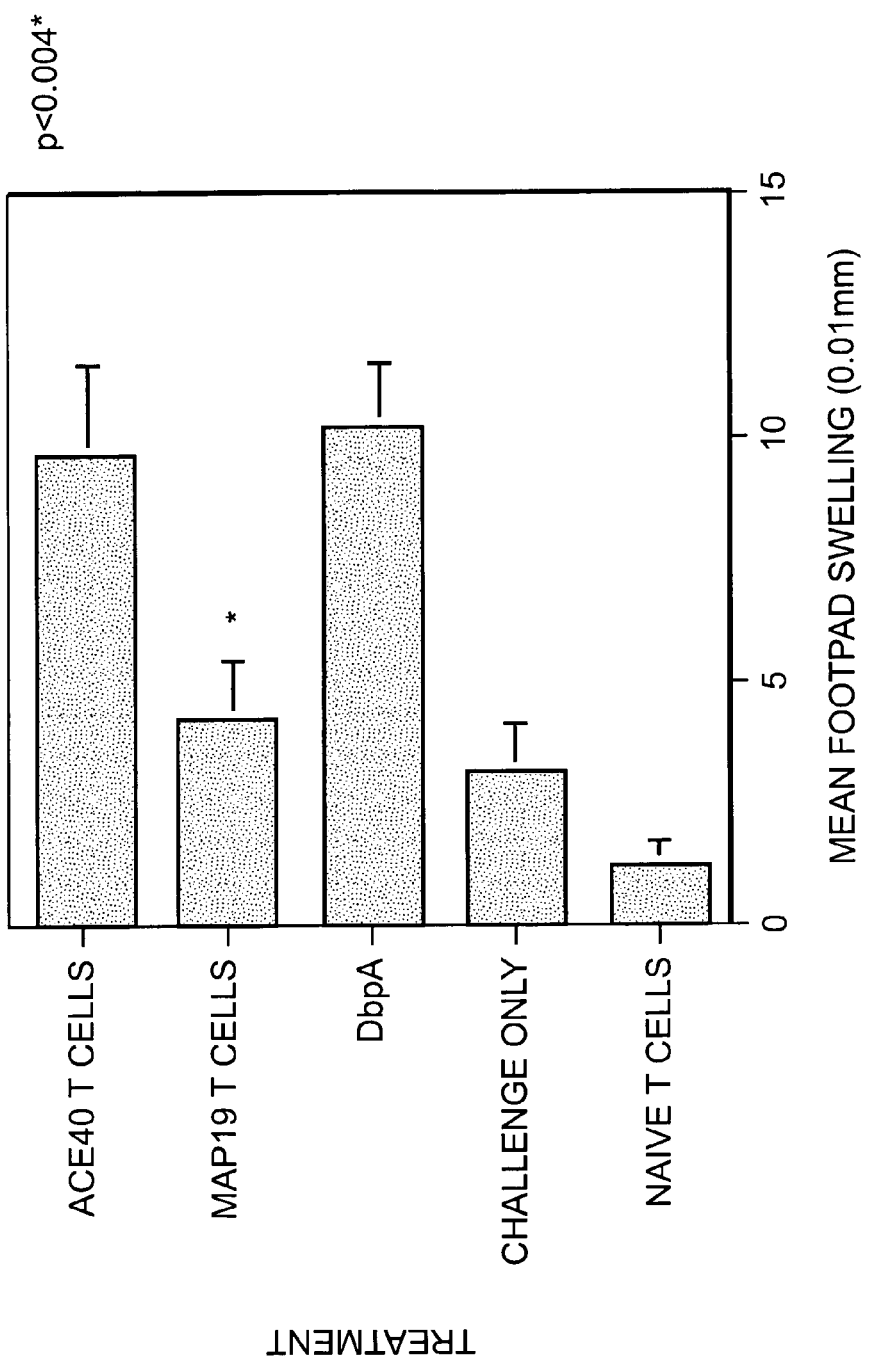

FIG. 3 is a graphic representation of tests showing that adoptively transferred T cells from Map-treated mice do not elicit a DTH response in naive mice. DbpA-immunized mice were treated with either Map19 or SdrF as described above. On day 7, mice were sacrificed and spleens were harvested and enriched for T cells by nylon wool purification. $5 \times 10^7$ cells were injected i.p. into syngeneic recipients. 24 h later, recipient mice were challenged with DbpA and the DTH response was assessed as described above. DbpA-immunized and DbpA-immunized, SdrF-treated mice developed a significant DTH response compared to unimmunized but challenged mice ($p<0.04$*; Student's t test). DbpA-immunized, Map19-treated mice had a significantly reduced DTH response compared to the other treatment groups ($p<0.001$**; Student's t test). Data are expressed as the mean±SE of 5 mice.

Figure 4:
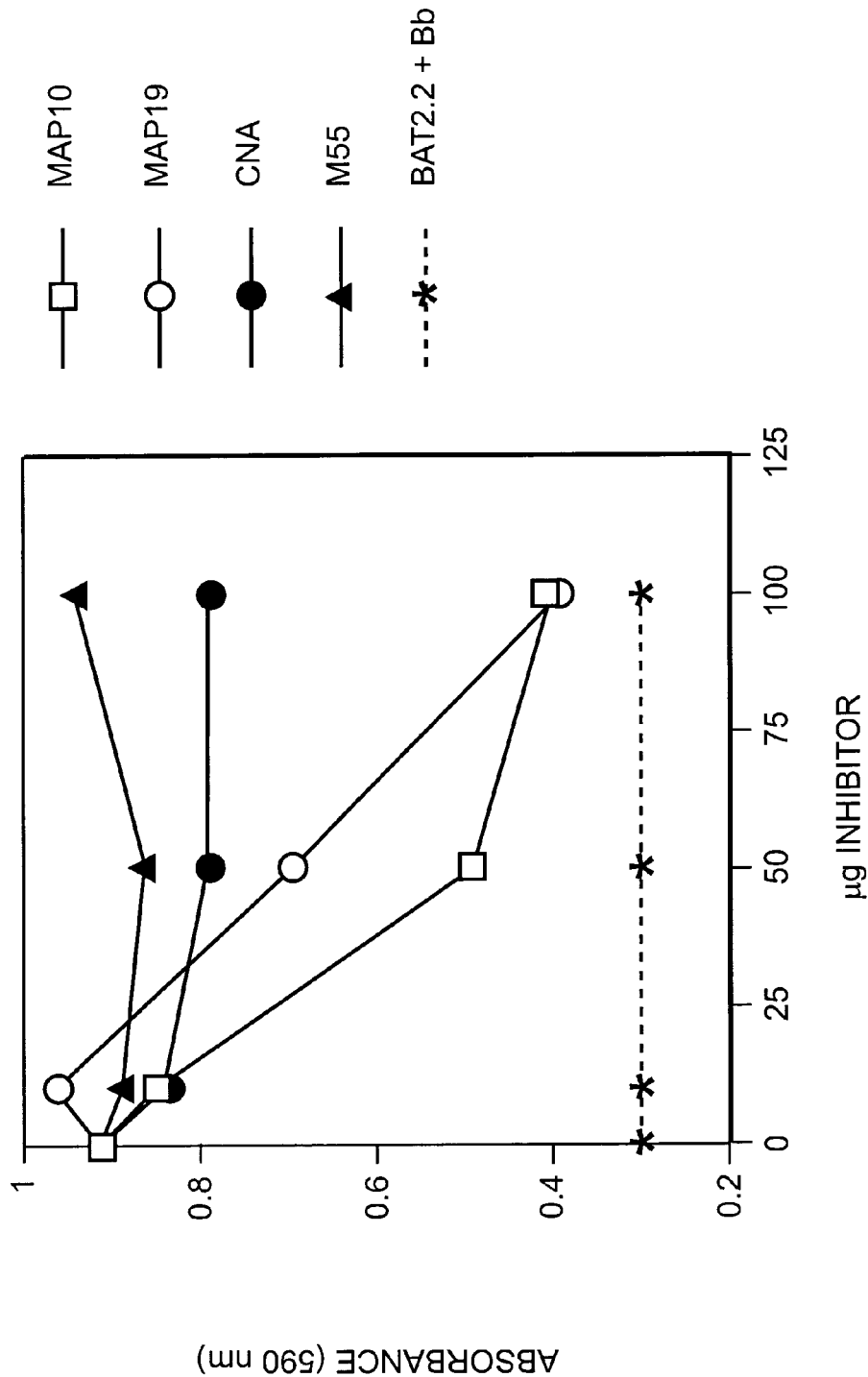

FIG. 4 is a graphic representation of the Map-induced inhibition of T cell proliferation using the method of the present invention. In this test, BAT2.2 T cell proliferation was measured after 40 h in culture in the presence of APCs and antigen in the presence of various proteins. 100 μg of each protein was added per well. Data are expressed as the mean absorbance±SE of triplicate wells.

Figure 5:
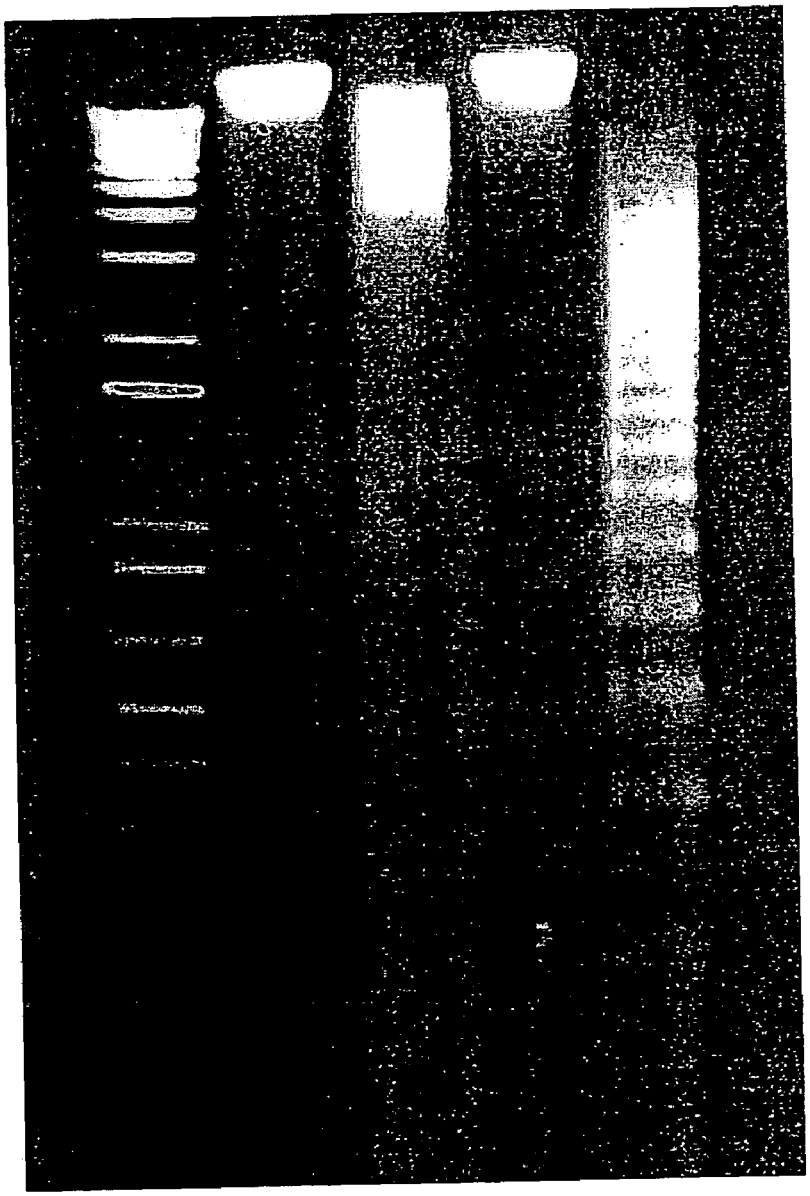

FIG. 5 shows Map-induced apoptosis of BAT2.2 T cells in accordance with the present invention. BAT2.2 cells (5 U IL-2/ml) were incubated in media alone (lane 1), or in the presence of either 100 μg Map19 (lane 2) or ACE40 (lane 3). DNA from U937 cells were used as a positive control (lane 5).

DETAILED DESCRIPTION OF THE PREFERRED EMBODIMENTS

In accordance with the present invention, there are provided methods and immunogenic compositions for suppressing, preventing or immunomodulating T cell-mediated responses in human or animal patients. In the preferred methods of the present invention, an effective amount of an isolated natural or recombinant Map protein or an active fragment or domain therefrom such as the Map10 or Map19 protein, is utilized in an amount effective to achieve such suppression or modulation. The MAP protein is a surface localized protein expressed by virtually every S. aureus strain. McGavin et al (7) originally identified the 72 kDa surface protein, from S. aureus strain FDA 574, that binds a variety of host proteins including BSP, fibrinogen, fibronectin, vitronectin, and thrombospondin. The gene, designated map, was cloned and sequenced (U.S. Pat. No. 5,648,240, incorporated herein by reference).

Reinfection of humans with SA is one of the hallmarks of diseases caused by this pathogen and the roles of acquired and innate immunity in protection against infection vary with the many manifestations of disease resulting from SA infections (25–28). While SA infections affecting the skin appear to be exacerbated by strong cellular responses, it is clear that cellular immunity is critical in orchestrating the clearance of systemic SA infections and in preventing reinfection with the same or similar pathogens (29–33). One possible reason for recurring SA infections is the reduction in chemotactic, phagocytic and bactericidal functions of polymorphonuclear leukocytes from patients with chronic or recurrent SA infections (27, 30, 33). Whether this is a function of the bacterial infection or a preexisting condition in these individuals is not known (27, 30, 33).

Regardless, the presence of SA-immunoregulatory molecules suggests that these bacteria have the potential to counteract or evade host defense mechanisms. Both superantigens and protein A produced by SA during an infection serve immune-evasion functions. Superantigens can activate between about 5–20% of T cells by directly binding to both the major histocompatibility complex (MHC) class II molecules on antigen-presenting cells and to the T cell receptor (TCR) on T cells. This interaction can initiate apoptosis in T cells and thymocytes in vivo and in vitro. The in vivo effects of such massive T cell stimulation often results in disease (e.g., toxic shock syndrome and food poisoning in humans) (34). Protein A, while less harmful to the host compared to superantigens, may also serve as a means of immune evasion by binding to the Fc fragment of immunoglobulins (i.e. IgG) resulting in loss of antibody function.

As described herein, the present inventors have shown that the Map protein and its effective regions or subdomains such as Map10 and Map19 appear to function as immune modulators with the capacity to affect host immune responses such as during SA infections. In accordance with the present invention, compositions containing the Map protein as described further below have the capacity to interfere with T cell activation and/or proliferation and can serve to potentiate survival in mammals of varied genetic backgrounds.

Studies in accordance with the present invention have shown that Map serves as an immunomodulatory protein as evidenced in double infection studies in which a primary infection with Map$^{31}$ SA conferred significant protection against reinfection with Map$^+$SA. This contrasts significantly with SA-induced pathology from mice receiving primary and secondary infections with Map$^+$SA. Accordingly, T cell-mediated responses in Map$^+$SA-infected mice appear to be abrogated by the presence of Map compared to Map$^-$SA-infected mice which develop cell-mediated immunity over the course of infection. Map$^-$SA infection, which is cleared over time, results in a memory response capable of controlling a secondary Map$^+$SA infection. That a primary Map$^-$SA infection conferred significant but not complete protection against Map$^+$SA challenge suggested that the delicate balance between an anamnestic response and Map-mediated immunomodulation could be affected by the challenge dose. Inhibition of DTH responses directly or as a result of adoptively transferred T cells from Map-treated mice combined with the in vitro effects of Map on T cell proliferation, have evidenced a direct involvement of Map with T cells resulting in apoptosis. Flow cytometric analysis of fluorescein isothiocyanate (FITC)-labeled Map19 revealed binding to 100% of BAT2.2 T cells.

Additional tests of nylon wool-purified naive T cells cultured in the presence of Map19 were not induced to either proliferate or undergo apoptosis. Furthermore, proliferation of naive T cells as a result of incubation with concanavalin A or by antibody-cross-linking of the TCR was not inhibited by Map. This result evidenced that activated T cells but not naive T cells are susceptible to Map and that T cell proliferation via 'non classical' pathways bypasses the Map-mediated inhibition of T cell proliferation. The present data provides evidence that Map functions as an immunoregulatory protein during SA infections and it appears that this protein is yet another weapon used by SA to escape immune recognition and clearance.

Accordingly, in accordance with the present invention, methods of utilizing an effective amount of the Map protein or its active regions or subdomains such as Map10 or Map19 are provided which can be used to treat or prevent T cell-mediated responses.

In addition, the administration of suppressive or immunomodulatory effective amounts of an isolated and/or purified *S. aureus* Map protein or one of its effective regions such as Map10 or Map19 can be utilized in methods of treating or preventing pathological conditions associated with overstimulation of T cells such as toxic shock syndrome. In accordance with the present invention, a method is provided which comprises administering to a human or animal patient in need of such treatment an effective amount of an isolated natural or recombinant Map protein. By Map protein is meant the whole natural or recombinant Map protein, or any effective or otherwise immunologically active fragment, fraction, domain, subdomain or region thereof which also has effective immunogenic properties so as to prevent or suppress a T cell-mediated response in the patient. In accordance with the invention, one such region is the Map19 protein, the nucleic acid sequence of which is provided herein as SEQ ID NO:1, and the amino acid sequence is provided as SEQ ID NO:2. Another such region is the Map10 protein, the nucleic acid sequence of which is provided herein as SEQ ID NO:3, and the amino acid sequence is provided as SEQ ID NO:4. Accordingly, the present invention also relates to methods of administering immunologically effective amounts of an isolated and/or purified *S. aureus* Map 10 or Map19 protein so as to be utilized in methods of treating or preventing pathological conditions associated with T cell proliferation or other T cell-mediated responses.

As would be recognized by one of ordinary skill in the art, compositions containing an effective amount of the Map protein, the Map10 protein or the Map19 protein can be prepared and administered to a human or animal patient in need of such treatment, particularly those patients requiring treatment or prevention of pathological conditions and other diseases associated with the T cell-mediated response.

By effective amount, it is recognized that the preferred dose for administration of a composition containing the Map, Map10 or Map19 protein in accordance with the present invention is that amount will be effective in preventing or modulating the T cell response, and one would readily recognize that this amount will vary greatly depending on the nature of the infection and the condition of a patient. Accordingly, an "effective amount" of the Map protein to be used in accordance with the invention is intended to mean a nontoxic but sufficient amount of the agent, such that the desired prophylactic, immunological or therapeutic effect is produced.

As one of skill in the art would recognize, the exact amount of an effective composition that is required will thus vary from subject to subject, depending on the species, age, and general condition of the subject, the severity of the condition being treated, the particular carrier or adjuvant being used and its mode of administration, and the like. Accordingly, the "effective amount" of any particular composition will vary based on the particular circumstances, and an appropriate effective amount may be determined in each case of application by one of ordinary skill in the art using only routine experimentation. For example, it is contemplated that an effective amount may be as little as about 15 μg in an application in order to achieve suppression of the T cell response, but this amount may be increased in cases wherein a higher dosage regimen is required. The dose should thus be adjusted to suit the individual to whom the composition is administered and will vary with age, weight and metabolism of the individual. The compositions may additionally contain stabilizers or pharmaceutically acceptable preservatives, such as thimerosal (ethyl(2-mercaptobenzoate-S)mercury sodium salt) (Sigma Chemical Company, St. Louis, Mo.).

The compositions of the invention may also be used as vaccines which will be useful in generating antibodies in a host patient which also may be useful to treat or preventing conditions associated with staphylococcal infection or T cell proliferation. As would be recognized by one skilled in this art, a vaccine may be prepared for administration in a number of suitable ways, such as by parenteral (i.e., intramuscular, intradermal or subcutaneous) administration or nasopharyngeal (i.e., intranasal) administration, and the general composition comprises the effective isolated Map, Map10 or Map19 protein along with a pharmaceutically acceptable vehicle, carrier or excipient. In one such mode, the vaccine is injected intramuscularly, e.g., into the deltoid muscle, however, the particular mode of administration will depend on the nature of the bacterial infection and the condition of the patient. In addition, antibodies from the Map protein may be obtained and isolated in conventional ways by the introduction of the appropriate Map protein in an appropriate host. In any event, the vaccines of the invention may be combined with any of a variety of pharmaceutically acceptable vehicles, carriers or excipients, such as water or a buffered saline, that are well known to those of ordinary skill in the art. In addition, the vaccine may be lyophilized for resuspension at the time of administration or in solution.

In carrying out the method of the present invention, isolation and/or purification of the Map protein or of the Map19 protein, or other active fragments or domains of the Map protein, can be accomplished in a number of suitable ways as would be recognized by one skilled in the art. For example, both the Map protein and the Map19 protein may be produced recombinantly using conventional techniques well known in the industry. With regard to the Map19 protein (SEQ ID NO: 2), one such suitable method would be through expression in *E. coli* (e.g., JM101 from Qiagen®, Chatsworth, Calif.) harboring the appropriate plasmid (11–16). In this method, *E. coli* was grown at 37° C. in LB containing the appropriate antibiotics until they reached an $A_{600}$ of 0.6 (17). Isopropyl-β-D-thiogalactopyranoside (IPTG) (Life Technologies) was added to a final concentration of 0.2 mM, and the cells were incubated at 37° C. for an additional 4 hours. Cells from a 1 L culture were harvested by centrifugation and resuspended in 10 ml "binding buffer" (BB) (20 mM Tris HCl, 0.5 M NaCl, 15 mM imidazole, pH 8.0) and lysed in a French pressure cell at 11,000 pounds/inch$^2$ (13). The lysate was centrifuged at 40,000×g for 15 min and the supernatant filtered through a 0.45 μm filter. A 1 ml iminodiacetic acid SEPHAROSE column (Sigma, St. Louis, Mo.) was charged with 75 mM $NiCl_2.6H_2O$ and equilibrated with BB. The filtered supernatant was applied to the column and washed with 10 volumes of BB, then 10 volumes of BB containing 60 mM imidazole.

The bound proteins were eluted with BB containing 200 mM imidazole, dialyzed against PBS containing 10 mM EDTA, then dialyzed against PBS (13). Protein concentrations were determined by the Bicinchoninic Acid (BCA) Protein Assay (Pierce) and proteins were stored at −20° C. until use.

In addition to obtaining isolates of the Map protein through recombinant means, natural isolates of the Map protein may be obtained for use in the present invention by a number of suitable means as well. For example, the natural Map protein can be extracted using standard methods. In one such suitable method, Map$^+$SA and Map$^-$SA were grown overnight as described above. Bacteria were pelleted by centrifugation and resuspended in 1 M LiCl (one tenth of the original media volume). The suspension was incubated at 42° C. with shaking for two hours. The bacteria were pelleted and the supernatant was removed and quantified for protein by UV spectrophotometry using 1 M LiCl as a blank. Extracted proteins were diluted to 0.2-mg/ml in PBS and passed through a 0.45-micron filter for sterilization prior to i.p. injection (7).

As indicated above, and in the examples below, the method of the present invention is carried out by administering effective amounts to human or animal patients so as to achieve the desired prophylactic, immunological or therapeutic effect via the suppression, reduction or modulation of the T cell response, and such effective amounts would be determined through routine means as indicated above for a particular patient based on factors such as type and size of patient, type of infection, level of virulence, etc. For example, it is contemplated that formulations with as little as 15 μg of an isolated Map protein, or Map10 or Map19, may be effective in achieving the suppression or modulation of the T cell response.

Map's ability to impede the development of cell-mediated immunity thus evidences that recombinant Map or formulations thereof as described above may have tremendous potential therapeutic value in a wide variety of clinical and pathologic conditions. For example, certain T cell lymphoproliferative diseases may be potentially treated with Map; these include thymoma, T lymphoblastic lymphoma, T chronic and acute lymphoblastic leukemia (20–30%), mycosis fungoides (Sezary's syndrome), T cell type of hairy cell leukemia, HTLV-associated Japanese, Caribbean and American adult T cell leukemia/lymphoma, and approximately 30% of non-Hodgkin's lymphomas (NHL). Non-Hodgkin's lymphoma is the fifth most frequent malignancy in the United States with more that 55,000 cases diagnosed in 1997. The incidence of this disease has increased 3–5% over the last two decades. A variety of treatments aimed at reducing cell proliferation and suppressing immune function in cases of lymphoproliferative diseases, in particular NHL, can include purine analogues, chemotherapy, surgery, glucocorticoids, α-2-recombinant interferon, and recombinant interferon γ(16–19).

In addition to neoplastic lymphoproliferative disorders, autoimmune lymphoproliferative syndrome associated with defects of the Fas gene result in uncontrolled activation of lymphocytes which lead to lymphadenopathy and progression of autoimmune disease. In murine models of autoimmunity, treatment with antibodies against T cells will retard disease progression as long as the treatment is continued, however, these treatments are not available to humans (20). In addition, long-term administration of agents such as anti-inflammatory agents, immunosuppressants, and cytotoxic agents that have previously been used to treat autoimmune disease such as systemic lupus erythromatosis and reactive arthritis can result in a plethora of side-effects.

Therapeutic applications for Map may also be available in various conditions resulting from microbial infections. While specific immunity to extracellular bacteria is primarily humoral in nature, T cell responses to extracellular microbes consist of $CD4^{+}$ T cells responding to antigens associated with MHC II molecules. Potential injurious consequences resulting from this type of infection are a result of bacterial toxins (super antigens) that can stimulate large numbers of $CD4^{+}$ T cells. These proliferating T cells can produce large quantities of cytokines that result in abnormalities that are similar to septic shock.

Patients who survive the critical phases of *Listeria monocytogenes* infections develop activated T lymphocytes that promote the formation of granulomas. Although both $CD4^{+}$ and $CD8^{+}$ T cells are activated during Listeriosis, the protective efficacy of $CD4^{+}$ cells is minor compared to that of $CD8^{+}$ cells. $CD4^{+}$ cells, however, are necessary for granuloma formation, DTH, and splenomegaly and their presence is closely associated with the production of cytokines in *Listeria*-induced antigen-specific inflammatory phenomena (21–23).

Specific immune responses to parasites (protozoa, helminthes, and ectoparasites) are usually $CD4^{+}$-mediated. In some cases, immune responses to parasites can also contribute to tissue injury. Some parasites and their byproducts can cause granuloma formation with concomitant fibrosis. The helminth *Schistosoma mansoni* release eggs into the blood stream, many of which remain lodged in the liver. The host immune response to the eggs is $CD4^{+}$-mediated and results in a DTH responses against the eggs followed by granuloma formation. Granuloma-associated fibrosis resulting from this immune response leads to disruption of venous blood flow in the liver, portal hypertension, and cirrhosis.

Alternate treatment modalities for modulating T cell responses gone awry is of significant concern since some treatments e.g. immunosuppressants and chemotherapy have detrimental side effects and some conditions resulting from bacterial infections (e.g. septic shock) do not have established treatment protocols.

Even further, the Map compositions in accordance with the present invention may be useful in treatment of T cell proliferative conditions such as poison ivy. In the preferred mode, the effective amount of the Map protein, or active regions such as Map10 or Map19, would be used in a cream or other dermatologically acceptable form and applied on the affected area.

In short, the present invention can thus be utilized advantageously as a means of treating or preventing pathological conditions associated with the T cell immune response and will be useful in suppressing or modulating the T cell-mediated responses in a human or animal patient so as to treat, prevent or ameliorate a wide variety of conditions caused by T cell-mediated responses.

EXAMPLES

The following examples are provided which exemplify aspects of the preferred embodiments of the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Overview

*Staphylococcus aureus* (SA) expresses a 72-kDa protein with the capacity to bind to a variety of extracellular matrix components (ECM), suggesting that at least one role for this protein involves adherence and colonization of host tissues. Analysis of Map, however, also revealed homologies to a segment of the peptide-binding groove of the b chain of the major histocompatability class (MHC) II mammalian proteins. Map-deficient SA (Map⁻ SA) were generated to examine Map's role in the infection process. Map⁻SA-infected mice presented with significantly reduced levels of arthritis, osteomylitis, and abscess formation compared to Map⁺SA-infected control animals. Furthermore, Map⁻SA-infected mice challenged with Map⁺SA were significantly protected against SA-induced pathology compared to mice infected and challenged with Map⁺. Native and recombinant forms of Map were tested for their ability to interfere with T cell response in vivo and in vitro. T cells or mice treated with recombinant Map had reduced levels of T cell proliferation and significant reduction of the delayed-type hypersensitivity (DTH) response to challenge antigen, respectively. The data presented here evidence a role for Map as an immunomodulatory protein which may play a role in persistent SA infections and thus may function to potentiate SA survival in mammals by affecting the host's cellular immune responses.

Background

*Staphylococcus aureus* (SA) is an opportunistic pathogen that can cause a wide spectrum of infections from superficial local skin infections to life-threatening systemic infections that can affect internal organs and tissues. In addition, bacterial arthritis, as well as acute and chronic osteomyelitis caused by haematogenous spread or by direct inoculation in open trauma or surgical intervention such as internal fixation or joint replacement, affect hundreds of thousands of patients each year (1–6). SA is also a major cause of infections associated with indwelling medical devices, such as catheters and prosthesis (6). The cost to society in patient care, which often involves extended hospital stays and repeated surgery, can be estimated at several billion dollars per year. With the documented emergence of multidrug resistance SA strains, the threat of this widely distributed pathogen is now appreciated and novel therapies for treatment and prevention are needed.

A search for SA adhesins recognizing host components uncovered a 72-kDa protein capable of binding a variety of host proteins (7). Cloning and sequencing of this gene revealed a protein consisting of 110-amino acid-long domains repeated six times with each domain containing a 31 amino acid-long subdomain with homology to MHC class II. If conservative amino acid substitutions were included, the respective subdomains were 61, 65, 52, 59, 52, and 45% similar to the amino-terminal end of the chain of many MHC class II proteins from different mammalian species (8).

The present work supports a role for Map as an immunomodulatory protein. Mice infected with SA genetically manipulated to be deficient in Map (Map⁻SA) have significantly reduced levels of arthritis and abscess formation (heart and kidneys) following reinfection with wild-type SA (Map⁺SA) compared to mice infected and reinfected with Map⁺SA or mice receiving a single inoculum of Map⁺SA. Evidence linking interactions between Map and T cells came from experiments in which nude mice were infected with Map⁻SA. The severity of osteomyelitis and arthritis was greater in nude mice compared to genotype controls infected with SA⁻Map, suggesting not only a role for T cells in protection against SA infections but also a role for Map in circumventing T cell-mediated immunity. Testing the hypothesis that Map acts to interfere with cellular immunity, various T cell-mediated responses were measured in vivo and in vitro in the presence of Map. DTH, which is a CD4⁺-mediated response, was significantly reduced in Map-treated mice and T cell proliferation in vitro was significantly reduced in the presence of Map, likely as a function of Map-induced apoptosis. These data evidence that Map is a virulence factor whose abilities to potentially alter T cell function in vivo may affect SA persistence and survival and may function in facilitating recurring SA infections.

Materials and Methods

Mice

Specific pathogen-free (MTV⁻) BALB/c and C3H/Hen mice were purchased from Harlan Sprague Dawley, Indianapolis, Ind. The animals were maintained in facilities approved by the American Association for Accreditation of Laboratory Animal Care in accordance with current regulations and standards of the United States Department of Agriculture, Department of Health and Human Services, and National Institutes of Health. All animal procedures were approved by the Institutional Animal Care and Use Committee. Female mice were 8–10 weeks old at the start of each experiment.

Expression and Purification of Recombinant Proteins

Recombinant Map19, DbpA SdrF, M55, CNA, ACE19 and ACE40 were expressed in *E. coli* (JM101) (Qiagen, Chatsworth, Calif.) harboring the appropriate plasmid (11–16). *E. coli* was grown at 37° C. in LB containing the appropriate antibiotics until they reached an $A_{600}$ of 0.6 (17). Isopropyl-β-D-thiogalactopyranoside (IPTG) (Life Technologies) was added to a final concentration of 0.2 mM, and the cells were incubated at 37° C. for an additional 4 hours. Cells from a 1 L culture were harvested by centrifugation and resuspended in 10 ml "binding buffer" (BB) (20 mM Tris HCl, 0.5 M NaCl, 15 mM imidazole, pH 8.0) and lysed in a French pressure cell at 11,000 pounds/inch² (13). The lysate was centrifuged at 40,000×g for 15 min and the supernatant filtered through a 0.45 µm filter. A 1 ml iminodiacetic acid Sepharose column (Sigma, St. Louis, Mo.) was charged with 75 mM $NiCl_2.6H_2O$ and equilibrated with BB. The filtered supernatant was applied to the column and washed with 10 volumes of BB, then 10 volumes of BB containing 60 mM imidazole. The bound proteins were eluted with BB containing 200 mM imidazole, dialyzed against PBS containing 10 mM EDTA, then dialyzed against PBS (13). Protein concentrations were determined by the Bicinchoninic Acid (BCA) Protein Assay (Pierce) and proteins were stored at –20° C. until use.

Quantitation of *S. aureus* and Intravenous Injections

Map⁺SA and Map⁻SA (strain Newman 8325) were grown overnight in Lennox broth (LB) (Difco, Detroit, Mich.) media at 37° C. with shaking and used in all infection experiments. 50 µl of this culture was used to inoculate 10 ml of fresh LB in a 250 ml Erlenmeyer flask. The new cultures were grown as above until the optical density reached 0.5 at 600 nm with a 1-cm quartz cuvette. Aliquots of each culture were quantified for colony forming units (CFU). The remainder of each culture was washed three times in sterile PBS. The cultures, based on prior growthcurve determinations, were diluted to approximate 2×10⁷ CFU/ml. Mice were in injected i.v. with 1×10⁷ *S. aureus* in 0.5 ml PBS and monitored for up to eight weeks. At the conclusion of the experiment, mice were sacrificed and the joints were examined histologically for arthritis development as described previously (18, 19).

Extraction of Map from *Staphylococcus aureus*

Map⁺SA and Map⁻SA were grown overnight as described above. Bacteria were pelleted by centrifugation and resuspended in 1 M LiCl (one tenth of the original media volume). The suspension was incubated at 42° C. with shaking for two hours. The bacteria were pelleted and the supernatant was removed and quantified for protein by UV spectrophotometry using 1 M LiCl as a blank. Extracted proteins were diluted to 0.2-mg/ml in PBS and passed through a 0.45-micron filter for sterilization prior to i.p. injection (7).

In vitro Proliferation of BAT2.2 T Cells

The *Borrelia burgdorferi*-specific T cell line BAT2.2 was stimulated with whole, inactive *Borrelia* and antigen presenting cells (APC) as described previously (18, 20). Briefly, 1×10⁵ BAT2.2 T cells were cultured in 96-well flat-bottom plates (Costar, Cambridge Mass.) along with 3×10⁵ mitomycin-treated APC in complete medium (CTL) (RPMI 1640 containing 2 mM L-glutamine, 100 units/ml penicillin, 100 µg/ml streptomycin, 50 µg/ml gentamicin, 0.2 mM nonessential amino acids, 11 µg/ml sodium pyruvate, 0.02 M N-2-hydroxyethylpiperaxine-N'-2ethanesulfonic acid, and 5×10⁵ N 2-mercaptoethanol+10% heat-inactivated fetal bovine serum), and *Borrelia* (2 µg) in the presence of various proteins. Each treatment group was done in triplicate in a final volume of 200 µl complete medium. 10, 50, and 100 µg of each protein was added to each well and the T cells were allowed to proliferate for 24–48 ours at 37° C. 4 h before the end of the proliferation period, 20 µl/well of 3-{4,5-Dimethylthizol-2-y}-2,5diphenyl-tetraxolium bromide (MTT) (5 mg/ml) was added to each well. After 4 h incubation at 37° C., 100 µl of solubilization buffer (0.04 N HCl in isopropanol) was added to each well and absorbance measured at 590 nm. Data are expressed as mean±SE of the mean of triplicate wells.

Delayed Type Hypersensitivity (DTH) Assay

Mice were immunized with 20 µg of decorin binding protein A (DbpA) in complete Freund's adjuvant (day 0) (19). 7 days post immunization, mice were challenged with 2.5 µg DbpA (13). DbpA was administered in 50 µl of PBS. At the time of immunization, days 2, 4, and 6 post immunization, mice were injected i.p. with 100 µg of native Map (N-Map) extracted from Map⁺SA, supernatant from Map⁻SA, or with 100 µg of the recombinant proteins Map19, SdrF, M55 or ACE40 in 500 µl of PBS (11–15, 21). The footpads were measured before challenge and 24 h later, using a spring-loaded micrometer (Mitutoyo, Tokyo, Japan). Mice were anesthetized with Metofane™ during footpad measurements (22).

Adoptive T Cell Transfer

BALB/c mice (5 mice/group) were immunized with DbpA and were treated with recombinant Map19 or recombinant ACE19 as described above. The day after the last Map19 or ACE40 treatment mice were sacrificed and the spleens from each treatment group were enriched for T cells by passage over nylon wool columns as described previously (20). 24 h after i.p. injection of T cells (5×10⁷ nylon wool-enriched T cells/mouse in 500 µl complete media), mice were challenged in the hind footpads with DbpA and the DTH response was assessed as described above.

Map-Induced Apoptosis of BAT2.2 Cells

2×10⁶ BAT2.2 T cells/well (5 U IL-2/ml) were incubated in the presence of Map19 or ACE19 in a final volume of 200 µl complete media and examined for apoptosis using an Apoptotic DNA Ladder Kit (Roche Molecular Biochemicals, Indianapolis, Ind.) according to manufacturers instructions. 100 µg of each protein was used and apoptosis measured after a 24 h incubation at 37° C. DNA was treated with 2 µg/ml RNase (DNase free) for 20 min. at room temperature before examination by agarose gel electrophoresis.

Flow Cytometry

Nylon wool enriched T cells (1×10⁶/tube) were washed in PBS containing 3% FBS and stained with the following monoclonal antibodies: fluorescein isothiocyanate (FITC)-conjugated anti-mouse CD8a (Ly2) and phycoerythrin (PE)-conjugated anti-mouse CD4 (L3T4) (PharMingen, San Diego, Calif.). The cells were incubated with the directly conjugated antibodies for 1 h at 4° C. and then washed and analyzed on a Coulter EpicProfile (Coulter Corp., Miami, Fla.).

Results

Experimental *S. aureus* Infection

Infection parameters that resulted in high degrees of arthritis incidence were used to examine what role Map played in SA infection (23). BALB/c mice were injected in the tail i.v. with 1×10⁷ SA and sacrificed 4 weeks later for histological examination of hind tibiotarsal joints. These preliminary experiments revealed that Map⁻SA-infected mice had both a reduced frequency and severity of arthritis compared to Map⁺SA-infected controls. The hypothesis that Map acted as an immunomodulator resulting in impaired immunity to SA with a concomitant inability to respond to a challenge infection was tested by infecting mice with Map⁻SA and Map⁺SA respectively, and challenging both groups with Map⁺SA 4 weeks later. Significant differences were observed in abscess formation in hearts and kidneys between the Map⁻/Map⁺-infected group and the Map⁺/Map⁺- and -/Map⁺-infected groups (Table I). Less than 50% of hearts and 25% of kidneys from Map⁻/Map⁺ infected mice presented with abscesses compared to >75% abscess formation in both hearts and kidneys from Map⁺/Map⁺ and -/Map⁺ infected mice (Table I). Significant differences were also observed in arthritis and osteomyelitis scores and frequencies (Table II). Arthritis was prevalent in 54% of mice infected with Map⁻/Map⁺ compared to >80% incidence in Map⁺/Map⁺ and -/Map⁺ infected mice (Table II). The mean arthritis and osteomyelitis scores recorded were also more than 2 times less in Map⁻/Map⁺ infected mice compared to scores from Map⁺/Map⁺- and -/Map⁺-infected mice (Table II).

Map-mediated Inhibition of Delayed-type-hypersensitivity (DTH)

Figure 1A:
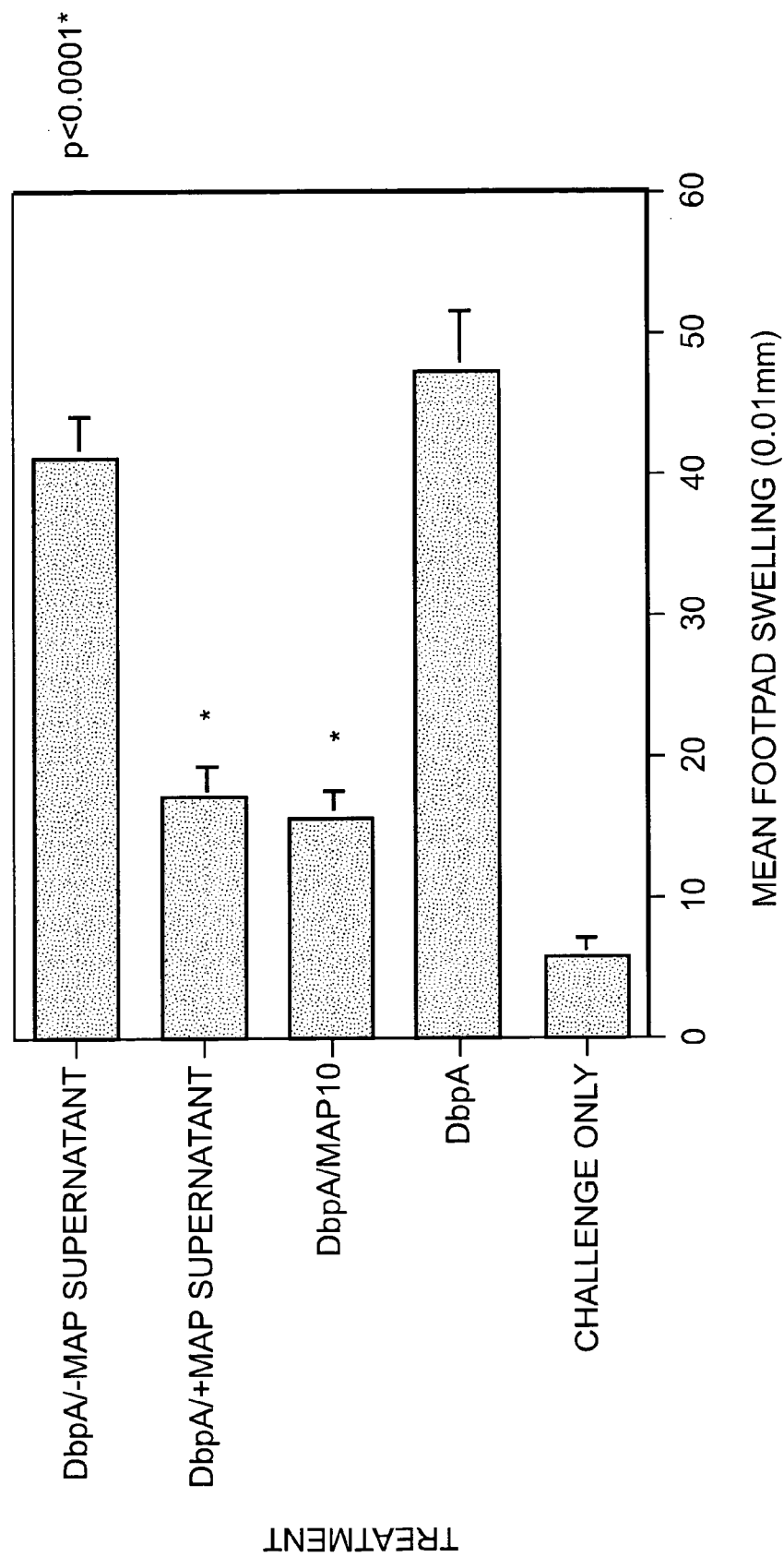
Figure 1B:
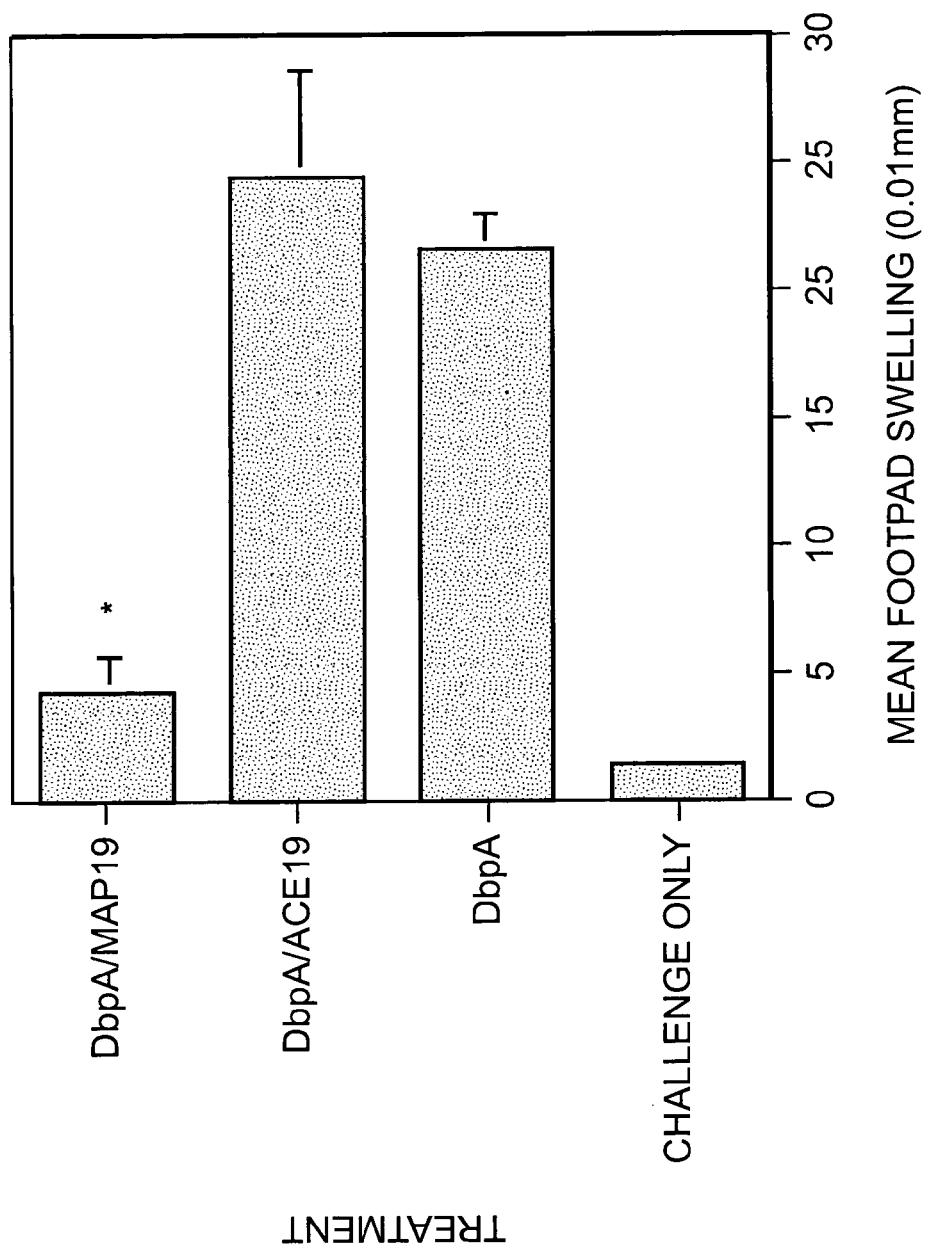
Figure 1C:
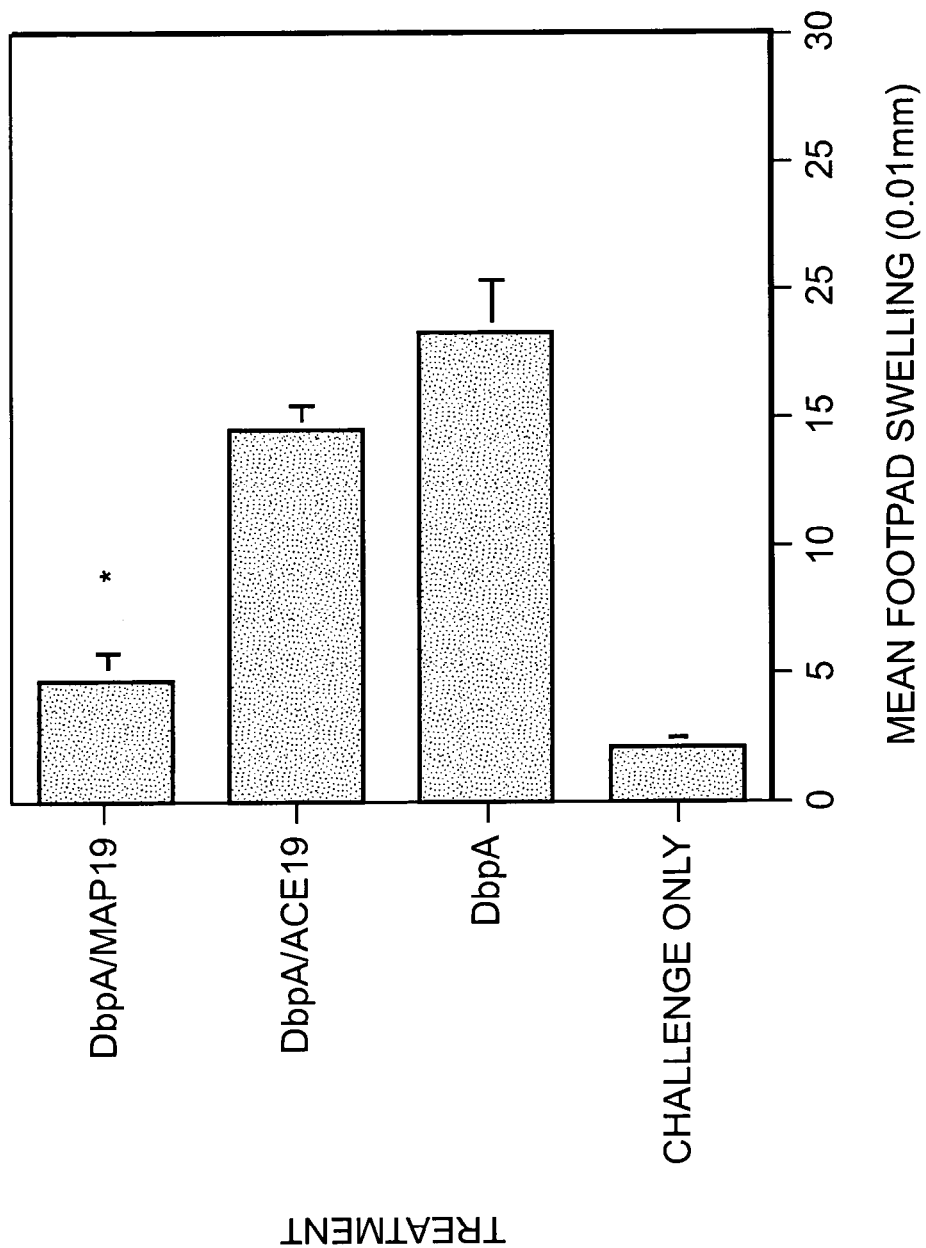

The similarity between Map and the peptide-binding region of class II MHC combined with the high levels of Map recoverable from the surface of SA prompted experiments designed to address the question regarding the potential role of Map on cellular immunity (7, 8). DTH responses are initiated and mediated by CD4⁺ T cells in response to recall antigens and result in specific, measurable inflammation at the site of challenge. Mice immunized with recombinant decorin-binding protein A (DbpA) emulsified in complete Freund's adjuvant (CFA) developed a significant DTH response to DbpA as measured by footpad swelling 7 days post immunization (FIG. 1) (19). However, mice treated with native Map (⁺Map Supernatant) or recombinant Map19 on the day of immunization (day 0) and days 2, 4 and 6 post immunization had a significantly reduced DTH response to DbpA compared to control mice (FIG. 1). Neither supernatants from Map⁻SA (FIG. 1a) or recombinant control protein ACE19 had any measurable effects on the DTH response to DbpA (FIGS. 1b–c). Map19's inhibitory effects were not affected by genetic differences since the DTH response was diminished in both BALB/c and C3H/Hen mice following immunization and challenge (FIGS. 1b and c, respectively).

Map Time Course and Dose Response for DTH Inhibition

Both the induction and elicitation of the DTH response were affected by Map treatment since Map19 injected either before or after immunization resulted in a significant reduction in the DTH response (Table III). Although all Map19-treated mice had a significantly reduced response to DbpA challenge following immunization, mice receiving Map19 on both the day of immunization and challenge (in addition to d2 and d4, Experiment I Table III) had the greatest reduction in footpad swelling compared to control mice (13.7±1.46 vs. 34.75±3.47 mm×$10^{-2}$, respectively) (Experiment I, Table III). The hypothesis that Map19 could act to prevent DTH by interfering with either the induction or elicitation of DTH was tested by comparing challenge responses in untreated mice to groups either treated with Map19 every other day (starting on the day of immunization) or to mice treated with Map19 only on the day of immunization and challenge (Experiment 2, Table III). Map19-treated mice had a significantly reduced DTH response compared to untreated or ACE40-treated controls (Experiment II, Table III). Since mice treated only on the days of immunization and challenge had a significantly reduced DTH response indistinguishable from the response observed in mice treated with Map19 every other day, it evidenced that Map19's inhibitory activity correlated with T cell activation and that it's capacity to interfere with T cell function was maximal during the T cell activation stages of DTH. Doses of Map in the excess of 100 µg did not further reduce the DTH response, however, 25 µg, the lowest dosed tested in this experiment, still significantly reduced the DTH response (FIG. 2).

Adoptively Transferred T Cells from Map-Treated Mice

Mice immunized with DbpA were either left untreated or injected i.p. with either Map19 or the recombinant control protein SdrF on the day of immunization (day 0) and on days 2, 4, and 6 post immunization. On day 7, mice were sacrificed and single cell suspensions from whole spleens were prepared and enriched for T cells by passage over nylon wool columns (20). Adoptive transfer of nylon wool-purified T cells from Map19-treated mice did not elicit a DTH response to DbpA in naive recipients compared to mice adoptively transferred with enriched T cells from control groups (FIG. 3). Flow cytometric analysis of cells nylon wool-collected cells revealed a profile that was 46.83±0.92% CD4⁺, 31.63±0.96% CD8⁺, 1.2±0.26% CD4⁺ CD8⁺, and 20.4±1.33% CD4⁻ CD8⁻. These data are expressed as the mean percentage of positive cells±SE for the 3 groups examined.

Inhibition of T Cell Proliferation and Apoptosis Induction in vitro.

Recombinant Map10 (SEQ ID NOS. 3 and 4) and Map19 (SEQ ID NOS. 1 and 2) were tested for their ability to inhibit the proliferation of the *Borrelia*-specific T cell line BAT 2.2 (8, 20). T cell proliferation was measured at 40 h after plating in the presence of mitomycin C-treated syngeneic antigen presenting cells (APC) and inactive *Borrelia* (iBb) (20). Proliferation was measured as a function of tetrazolium blue production following a 4 h incubation in the presence of MTT. BAT 2.2 cells in the presence of either Map10 or 19 but not in the presence of recombinant control proteins CNA or M55 were inhibited from proliferating (FIG. 4) (24). BAT 2.2 incubated in the presence of *Borrelia* only were plotted as baseline as the control group with the highest background proliferation (FIG. 4). In a similar experiment, BAT2.2 cells in the presence of IL-2 were cultured in the presence of Map19 for 24 h. DNA extracted from BAT2.2 T cells incubated in the presence of Map19 was examined for fragmentation by gel electrophoresis (FIG. 5). DNA fragmentation comparable to apoptotic-positive control DNA (lane 5) was only observed in DNA extracted from Map19-treated T cells (lane 3) but not untreated (lane 2) or ACE40-treated (lane 4) T cells (FIG. 5).

Summary

Reinfection of humans with SA is one of the hallmarks of diseases caused by this pathogen and the roles of acquired and innate immunity in protection against infection vary with the many manifestation of disease resulting from SA infections (25–28). While SA infections affecting the skin appear to be exacerbated by strong cellular responses, it is clear that cellular immunity is critical in orchestrating the clearance of systemic SA infections and in preventing reinfection with the same or similar pathogens (29–33). One possible reason for recurring SA infections is the reduction in chemotactic, phagocytic and bactericidal functions of polymorphonuclear leukocytes from patients with chronic or recurrent SA infections (27, 30, 33). Whether this is a function of the bacterial infection or a preexisting condition in these individuals is not known (27, 30, 33). Regardless, the presence of SA-immunoregulatory molecules suggests that these bacteria have the potential to counteract or evade host defense mechanisms. Both superantigens and protein A produced by SA during an infection serve immune-evasion functions. Superantigens can activate between 5–20% of T cells by directly binding to both the major histocompatibility complex (MHC) class II molecules on antigen-presenting cells and to the T cell receptor (TCR) on T cells. This interaction can initiate apoptosis in T cells and thymocytes in vivo and in vitro. The in vivo effects of such massive T cell stimulation often results in disease (i.e. toxic shock syndrome and food poising in humans) (34). Protein A, while less harmful to the host compared to superantigens, may also serve as a means of immune evasion by binding to the Fc fragment of immunoglobulins (i.e. IgG) resulting in loss of antibody function.

The present series of tests supported the idea that Map may function as an immune modulator with the capacity to affect host immune responses during SA infections. In addition to its potential role as a bacterial adhesin; our tests showed that Map apparently has the capacity to interfere with T cell activation and/or proliferation facilitating SA survival in mammals (8, 11, 24, 35, 36). Sequence analysis of the SA genome revealed 5 open-reading frames encoding Map-like proteins (14). While only one of these Map proteins (SA1751) had a >80% homology to Newman stain Map (8, 14), the presence of other Map-like proteins suggested a critical role for Map in SA survival; perhaps the potential to encode a variety of MHC II-like proteins can serve to potentiate survival in mammals of varied genetic backgrounds.

Additional evidence suggesting Map serves as an immunomodulatory protein stemmed from double infection studies in which a primary infection with Map⁻SA conferred significant protection against reinfection with Map⁺SA. This contrasts significantly with SA-induced pathology from mice receiving primary and secondary infections with Map$^+$ SA. Accordingly, it appears that T cell-mediated responses in Map$^+$SA-infected mice are abrogated by the presence of Map compared to Map$^-$SA-infected mice which develop cell-mediated immunity over the course of infection. Map$^-$ SA infection, which is cleared over time, results in a memory response capable of controlling a secondary Map$^+$SA infection. That a primary Map$^-$SA infection conferred significant but not complete protection against Map$^+$SA challenge suggested that the delicate balance between an anamnestic response and Map-mediated immunomodulation could be affected by the challenge dose. Our tests showed inhibition of DTH responses directly or as a result of adoptively transferred T cells from Map-treated mice, and this combined with the in vitro effects of Map on T cell proliferation evidenced a direct involvement of Map with T cells resulting in apoptosis. Flow cytometric analysis of fluorescein isothiocyanate (FITC)-labeled Map19 revealed binding to 100% of BAT2.2 T cells (data not shown).

In additional tests evidencing the effect on the Map protein on T cell-mediated responses, nylon wool-purified naive T cells cultured in the presence of Map19 were not induced to either proliferate or undergo apoptosis. Furthermore, proliferation of naive T cells as a result of incubation with concanavalin A or by antibody-cross-linking of the TCR was not inhibited by Map. This evidence that activated T cells but not naive T cells are susceptible to Map and that T cell proliferation via 'non classical' pathways bypasses the Map-mediated inhibition of T cell proliferation. Based on Map's effects on cellular immune responses in vivo and in vitro, it appears that this protein is yet another weapon used by SA to escape immune recognition and clearance. Accordingly, in accordance with the present invention, the administration of effective amounts of the Map protein or its active regions or fragments such as Map19 appears to be useful in achieving the suppression or modulation of T cell-mediated responses to a host cell against *S. aureus* and thus may be useful in methods to prevent or reduce the persistence or virulence of infection by staphylococcal bacteria.

Example 2

Tests of Map, Map10 and Map19

Materials and Methods

Mice

Specific pathogen-free ($MTV^-$) BALB/c were purchased from Harlan Sprague Dawley, Indianapolis, Ind. The animals were maintained in facilities approved by the American Association for Accreditation of Laboratory Animal Care in accordance with current regulations and standards of the United States Department of Agriculture, Department of Health and Human Services, and National Institutes of Health. All animal procedures were approved by the Institutional Animal Care and Use Committee. Female mice were 8–10 weeks old at the start of each experiment.

Quantitation of *S. aureus* and Intravenous Injections $Map^+$SA and $Map^-$ SA (strain Newman or 8325) were grown overnight in Lennox broth (LB) (Difco, Detroit, Mich.) media at 37° C. with shaking. 50 μl of this culture was used to inoculate 10 ml of fresh LB in a 250 ml Erlenmeyer flask. The new cultures were grown as above until the optical density reached 0.5 at 600 nm with a 1-cm quartz cuvette. Aliquots of each culture were quantified for colony forming units (CFU). The remainder of each culture was washed three times in sterile PBS. The cultures, based on prior growth-curve determinations, were diluted to approximate $2\times10^7$ or $2\times10^6$ CFU/ml. CFU was determined for each of the diluted cultures. Mice were in injected i.v. with either $5\times10^6$ or $1\times10^7$ *S. aureus* in 0.5 ml PBS and monitored for 4 weeks. At the conclusion of the experiment mice were sacrificed and the joints were examined histologically for arthritis development as described previously (14).

Extraction of Map from *Staphylococcus aureus*

$Map^+$ SA and $Map^-$ SA strain Newman were grown overnight with shaking in LB media. Bacteria were pelleted by centrifugation and resuspended in 1 M NaCl (one tenth of the original media volume). The suspension was incubated at 42° C. with shaking for two hours. The bacteria were pelleted and the supernatant was removed and quantified for protein by UV spectrophotometry using 1 M NaCl as a blank. Extracted proteins were diluted to 0.2-mg/ml in PBS and passed through a 0.45-micron filter for sterilization prior to i.p. injections. Final NaCl concentrations of the diluted extracts approximated twice that of physiologic conditions (320 mM compared to 150 mM) since the original extracts were usually diluted 1:5.

In vitro Proliferation of BAT2.2 T Cells

The *Borrelia burgdorferi*-specific T cell line BAT2.2 was stimulated with whole, inactive *Borrelia* and antigen presenting cells (APC) as described previously (14). Briefly, $1\times10^5$ BAT2.2 T cells were cultured in 96-well flat-bottom plates (Costar, Cambridgem Mass.) along with $3\times10^5$ mitomycin-treated APC in complete medium (RPMI 1640 containing 2 mM L-glutamine, 100 units/ml penicillin, 100 μg/ml streptomycin, 50 μg/ml gentamicin, 0.2 mM nonessential amino acids, 11 μg/ml sodium pyruvate, 0.02 M N-2-hydroxyethylpiperaxine-N'-2ethanesulfonic acid, and $5\times10^{-5}$ N 2-mercaptoethanol+10% heat-inactivated fetal bovine serum), and *Borrelia* (2 μg) in the presence of various proteins. Each treatment group was done in triplicate in a final volume of 200 μl complete medium. 10, 50, and 100 μg of each protein was added to each well and the T cells were allowed to proliferate for 40–72 hours at 37° C. 4 h before the end of the proliferation period, 20 μl/well of 3-{4,5-Dimethylthizol-2-y}-2,5diphenyl-tetraxolium bromide (MTT) (5 mg/ml) was added to each well. After 4 h incubation at 37° C., 100 μl of solubilization buffer (0.04 N HCl in isopropanol) was added to each well and absorbance measured at 570 nm. Data are expressed as mean±SE of the mean of triplicate wells.

Delayed Type Hypersensitivity (DTH) Assay

Mice were immunized with 20 μg of decorin binding protein A (DbpA) in complete Freund's adjuvant. 7 days post immunization, mice were challenged with 2.5 μg DbpA. DbpA was administered in 50 μl of PBS. At the time of immunization, days 3, 5, and 7 post immunization, mice were injected i.p. in 500 μl of PBS with 100 μg of native Map (N-Map) extracted from $Map^+$ SA, supernatant from $Map^-$SA, or the recombinant proteins Map 10 or SdrF. The footpads were measured before challenge and 24 h later, using a spring-loaded micrometer (Mitutoyo, Tokyo, Japan). Mice were anesthetized with Metofane™ during footpad measurements.

Expression and Purification of Recombinant Proteins

Recombinant Map19, DbpA SdrF, M55, CNA, ACE19 and ACE40 were expressed in *E. coli* (JM101) (Qiagen®, Chatswodh, Calif.) harboring the appropriate plasmid (11–16). *E. coli* was grown at 37° C. in LB containing the appropriate antibiotics until they reached an $A_{600}$ of 0.6 (17). Isopropyl-β-D-thiogaiactopyranoside (IPTG) (Life Technologies) was added to a final concentration of 0.2 mM, and the cells were incubated at 37° C. for an additional 4 hours. Cells from a 1 L culture were harvested by centrifugation and resuspended in 10 ml "binding buffer" (BB) (20 mM Tris HCl, 0.5 M NaCl, 15 mM imidazole, pH 8.0) and lysed in a French pressure cell at 11,000 pounds/inch$^2$ (13). The lysate was centrifuged at 40,000×g for 15 mm and the supematant filtered through a 0.45 pm filter. A 1 ml iminodiacetic acid SEPHAROSE column (Sigma, St. Louis, Mo.) was charged with 75 mM NiCl$_2$ 6H$_2$O and equilibrated with BB. The filtered supematant was applied to the column and washed with 10 volumes of BB, then 10 volumes of BB containing 60 mM imidazole. The bound proteins were eluted with BB containing 200 mM imidazole, dialyzed against PBS containing 10 mM EDTA, then dialyzed against PBS (13). Protein concentrations were determined by the Bicinchoninic Acid (BCA) Protein Assay (Pierce) and proteins were stored at −20° C. until use.

Map-Induced Apoptosis of BAT2.2 Cells $2 \times 10^6$ BAT2.2 T cells/well (5 U IL-2/ml) were incubated in the presence of either anti-T cell receptor chain antibody (5 or 10 μg/well) (clone H57-597, Pharmingen, San Diego, Calif.), Map10, Map19, or M55 in a final volume of 200 μl complete media and examined for apoptosis using an Apoptotic DNA Ladder Kit (Roche Molecular Biochemicals, Indianapolis, Ind.) according to manufacturers instructions. 100 μg of each protein was used and apoptosis measured after a 24 h incubation at 37° C. DNA was treated with 2 μg/ml RNase (DNase free) for 20 min. at room temperature before examination by agarose gel electrophoresis.

Adoptive T Cell Transfer

BALB/c mice (5 mice/group) were immunized with DbpA and were treated with recombinant Map10 or recombinant SdrF as described above. The day after the last Map10 or SdrF treatment (day 8 post immunization) mice were sacrificed and the spleens from each treatment group were enriched for T cells by passage over nylon wool columns as described previously (14). 24 h after i.p. injection of T cells ($5 \times 10^7$ nylon wool-enriched T cells/mouse in 500 μl complete media), mice were challenged in the hind footpads with DbpA and the DTH response was assessed as described above.

Flow Cytometry

Nylon wool enriched T cells ($1 \times 10^6$/tube) were washed in PBS containing 3% FBS and stained with the following monoclonal antibodies: fluorescein isothiocyanate (FITC)-conjugated anti-mouse CD8a (Ly2) and phycoerythrin (PE)-conjugated anti-mouse CD4(L3T4) (PharMingen, San Diego, Calif.). The cells were incubated with the directly conjugated antibodies for 1 h at 4° C. and then washed and analyzed on a Coulter EpicProfile (Coulter Corp., Miami, Fla.).

Results

Experimental *S. aureus* Infection

Map$^+$ or Map$^-$ strains of SA Newman or 8325 were administered i.v. to BALB/c mice and monitored for four weeks. Mortality between groups over a 4 week period was similar, however, arthritis development was significantly different between groups. Mice infected with Map$^-$ SA had a mean arthritis score of 0.5 and an arthritis incidence of 50%, compared to an arthritis score of 2.35 and 2.25 for Map$^+$ strains Newman and 8325, respectively. The incidence of arthritis was also 75% in mice infected with Map$^+$ SA, however only Map$^+$ Newman strain-infected mice developed sever osteomyelitis (75%) compared to mice from other groups (0%). Furthermore, spleens harvested from strain Newman Map$^+$ SA-infected mice were significantly larger than spleens isolated from mice infected with strain Newman Map$^-$ SA four weeks post infection.

Inhibition of T Cell Proliferation in vitro.

Recombinant Map 10 and Map 19 were tested for their ability to inhibit the proliferation of the *Borrelia*-specific T cell line BAT 2.2 (13, 14). T cell proliferation was measured at 40 and 49 h after plating in the presence of mitomycin C-treated syngeneic antigen presenting cells (APC) and inactive *Borrelia* (iBb) (14). Proliferation was measured as a function of tetrazolium blue production following a 4 h incubation in the presence of MTT. BAT 2.2 cells in the presence of either Map10 or 19 but not in the presence of recombinant control proteins CNA or M55 were inhibited from proliferating (3). BAT 2.2 incubated in the presence of *Borrelia* only were plotted as baseline since this control group had the highest background proliferation.

Inhibition of T Cell Activity in vivo.

N-Map and recombinant Map 10 were tested for their ability to interfere with the elicitation of a DTH response to DbpA in DbpA-immunized mice. On the day of immunization and on days 3, 5, and 7 post immunization mice were injected i.p. with 100 μg (500 μl) of either N-Map, Map supernatant, Map 10, or SdrF. At day 7 post immunization, mice from all groups were challenged in the hind footpads with 2.5 μg iBb. Footpads were measured 0 and 24 h post challenge. Mice treated with either N-Map or Map 10 had a significantly reduced DTH response to DbpA compared to untreated, Map$^-$ supernatant or SdrF-treated mice.

Adoptively Transferred T Cells from Map-Treated Mice do not Elicit a DTH

Mice immunized with DbpA were either left untreated or injected i.p. with either Map 10 or the recombinant control protein SdrF on the day of immunization and on days 3, 5, and 7 post immunization. On day 8, mice were sacrificed and single cell suspensions from whole spleens were prepared and enriched for T cells by passage over nylon wool columns (14). Adoptive transfer of nylon wool purified T cells from Map 10-treated mice did not elicit a DTH response to DbpA in naïve recipients compared to mice-adoptively transferred with enriched T cells from control groups. Flow cytometric analysis of cells nylon wool-collected cells revealed a profile that was 46.83±0.92% CD4$^+$, 31.63±0.96% CD8$^+$, 1.2±0.26% CD4$^+$ CD8$^+$, and 20.4±1.33% CD4$^-$CD8$^-$. These data are expressed as the mean percentage of positive cells±SE for the 3 groups examined.

TABLE I

Abscess formation in heart and kidneys harvested from Map⁻ and Map⁺ SA-infected mice[A]

| Infecting Strains | Tissue Examined[B] | |
|---|---|---|
| | Heart | Kidneys |
| Map−/Map+ | 12/26 (46%)[C,D] | 13/52 (25%)[E] |
| Map+/Map+ | 17/19 (89%) | 33/38 (86%) |
| −/Map+ | 29/31 (94%) | 48/62 (77%) |

[A]BALB/c mice were infected i.v. with either $1 \times 10^7$ Map⁺ or Map⁻ SA strain Newman or left untreated. 4 weeks post primary infection, mice from all groups received $1 \times 10^7$ Map⁺ SA i.v. 4 weeks latter hearts and kidneys were examined grossly and histologically for abscess formation.
[B]The data are pooled observations from three separate experiments.
[C]$p < .005$ versus Map⁺/Map⁺ group; Fisher's exact test.
[D]$p < .0001$ versus −/Map⁺; Fisher's exact test.
[E]$p < .0001$ versus Map⁺/Map⁺ and −Map⁺ groups; Fisher's exact test.

TABLE II

Histological examination of joints harvested from Map⁻ and Map⁺ SA-infected mice[A]

| Infecting Strains | Mean Arthritis Rating | Arthritis Frequency (%) | Mean Ostomylitis Score | Osteomyelitis Frequency (%) |
|---|---|---|---|---|
| Map−/Map+ | 0.84[B] | 14/26 (54%)[C] | 0.57[B] | 6/26[D] (23%) |
| Map+/Map+ | 1.65 | 18/21 (86%) | 1.95 | 14/21 (66%) |
| −/Map+ | 2.06 | 28/32 (88%) | 1.48 | 14/32 (44%) |

[A]BALB/c mice were infected i.v. with either $1 \times 10^7$ Map⁻ or Map⁺ SA strain Newman or left untreated. 4 weeks post primary infection, mice from all groups received $1 \times 10^7$ Map⁺ SA i.v. 4 weeks latter, the right hind limb joint was harvested and examined histologically for arthritis and osteomylitis.
[B]$p < 0.05$ versus control groups; Student's t test.
[C]$p < 0.05$ versus control groups; Fisher's exact test.
[D]$p < 0.005$ versus +Map/+Map group; Fisher's exact test.

TABLE III

Histological examination of joints harvested from SA⁻ Map or SA⁺ Map-infected nude mice[A]

| Infecting Strains | Mean Arthritis Rating | Arthritis Frequency (%) | Mean Ostomylitis Score | Osteomyelitis Frequency (%) |
|---|---|---|---|---|
| nu/+/Map⁺SA | 2.86 | 7/7 (100%) | 2.29 | 5/7 (71%) |
| nu/+/Map⁻SA | 1.33 | 8/9 (89%)[C] | 0.44[B] | 3/9 (33%) |
| nu/nu/Map⁺SA | 2.43 | 8/8 (100%) | 2.62 | 8/8 (100%) |
| nu/nu/Map⁻SA | 2.10 | 7/10 (70%) | 1.20 | 6/10 (60%) |

[A]Hsd nu/nu and nu/+ mice were infected i.v. with either $1 \times 10^7$ Map⁻ or Map⁺ SA strain Newman or left untreated. 4 weeks post primary infection, mice from all groups received $1 \times 10^7$ Map⁺ SA i.v. 4 weeks latter, the right hind limb joint was harvested and examined histologically for arthritis and osteomylitis.
[B]$p < 0.05$ versus nu/+/Map⁺ SA; Student's t test.

TABLE IV

The Effect of Map19 Treatment at Various Times Before and After Immunization on the Elicitation of DTH[A]

| Treatment[B] | Time Course | | | | | | | Mean Footpad Swelling[C] | SE[D] |
|---|---|---|---|---|---|---|---|---|---|
| Exp. I | d-6 | d-4 | d-2 | d0[E] | d2 | d4 | d7[F] | | |
| Map19 | + | + | + | +IM |   |   | CH | 18.75[G] | ±3.26 |
| Map19 |   | + | + | +IM |   |   | CH | 22.75[G] | ±2.66 |
| Map19 |   |   | + | +IM |   |   | CH | 20.25[G] | ±1.93 |
| Map19 |   |   |   | +IM |   |   | CH | 23.00[G] | ±1.36 |
| Map19 |   |   |   | +IM | + |   | CH | 17.75[H] | ±2.06 |
| Map19 |   |   |   | +IM | + | + | CH | 23.62[G] | ±3.48 |
| Map19 |   |   |   | +IM | + | + | +CH | 13.75[I] | ±1.46 |
| — |   |   |   |   |   |   | CH | 5.50[I] | ±1.24 |
| — |   |   |   | IM |   |   | CH | 34.75 | ±3.47 |
| Exp. II |   |   |   |   |   |   |   |   |   |
| Map19 |   |   |   | +IM | + | + | +CH | 13.30[I] | ±1.50 |
| Map19 |   |   |   | +IM |   |   | +CH | 10.10[I] | ±0.82 |
| ACE40 |   |   |   | +IM | + | + | +CH | 26.60[J] | ±2.83 |
| ACE40 |   |   |   | +IM |   |   | +CH | 26.75[J] | ±1.73 |
| — |   |   |   |   |   |   | CH | 3.10[I] | ±0.67 |
| — |   |   |   | IM |   |   | CH | 33.56 | ±3.04 |

[A]BALB/c mice were immunized with DbpA on day zero.
[B]+ Indicates treatment with 100 μg of recombinant Map19 at various time points prior to and after immunization. Control mice in Exp I were treated with ACE40 in a parallel experiment and had DTH responses similar to control mice (data not shown).
[C]Footpads were measured at 0 and 24 h after challenge. The data are expressed as the mean footpad swelling of five mice/group.
[D]Standard Error
[E]Mice were immunized with 5 μg of DbpA emulsified in CFA i.p.
[F]7 days after immunization the mice were challenged in both hind footpads with 2 μg of DpbA in 50 μl of PBS.
[G]$p < 0.05$; Students t test compared to IM and CH control.
[H]$p < 0.005$; Students t test compared to IM and CH control.
[I]$p < 0.0001$; Students t test compared to IM and CH control.
[J]Not significant compared to IM and CH control.

REFERENCES

1. Gristina et al. 1985. Molecular mechanisms in musculoskeletal sepsis. In AAOS Instructional Course Lectures. Vol. 39. W. Green, editor. Amer. Acad. Orthopedic Surgeons, Chicago. 471–486.

2. Gristina et al. Molecular mechanisms in musculoskeletal sepsis: the race for the surface. *Instr Course Lect.* 39:471–482.

3. Gillespie, W. J. 1989. Haematogenous osteomyelitis. In Orthopaedic Infections. R. D. D'Ambrosia, and R. L. Marier, editors. Slack Inc., Thorofare, N.J. 1–30.

4. Gustilo, R. B. 1989. Management of open fractures. In Current Concepts in the Management of Musculoskeletal Infections. R. B. Gustilo, R. P. Gruninger, and P. K. Peterson, editors. W. B. Sanders Co., Philadelphia. 87–117.

5. Nelson, J. P. 1989. Prevention of postoperative infection by airborne bacteria. In Current Concepts in the Management of Musculoskeletal Infections. R. B. Gustilo, R. P. Gruninger, and P. K. Peterson, editors. W. B. Sanders Co., Philadelphia. 75–80.

6. Rupp, M. E. 1997. In The Staphylococci in Human Disease. K. B. Crossley, and G. L. Archer, editors. Churchill Liningstone, New York. 379–399.

7. McGavin et al. 1993. Identification of a *Staphylococcus aureus* extracellular matrix-binding protein with broad specificity. *Infect Immun.* 61:2479–85.

8. Jonsson et al. 1995. *Staphylococcus aureus* expresses a major histocompatibility complex class II analog. *J Biol Chem.* 270:21457–21460.

9. Jahreis et al. 2000. Effects of two novel cationic staphylococcal proteins (NP-tase and p70)and enterotoxin B on IgE synthesis and interleukin-4 and interferon-gamma production in patients with atopic dermatitis. *Br J Dermatol.* 142:680–687.

10. Jahreis et al. 1995. Two novel cationic staphylococcal proteins induce IL-2 secretion, proliferation and immunoglobulin synthesis in peripheral blood mononuclear cells (PBMC) of both healthy controls and patients with common variable immunodeficiency (CVID). *Clin Exp Immunol.* 100:406–411.

11. Patti et al. 1994. The *Staphylococcus aureus* collagen adhesin is a virulence determinant in experimental septic arthritis. *Infect Immun.* 62:152–161.

12. Joh et al. 1994. Fibronectin receptors from gram-positive bacteria: comparison of active sites. *Biochemistry.* 33:6086–6092.

13. Guo et al. 1998. Decorin-binding adhesins from *Borrelia burgdorferi*. *Mol Microbiol.* 30:711–723.

14. Kuroda et al. 2001. Whole genome sequencing of methicillin-resistant *Staphylococcus aureus*. *Lancet.* 357:1225–1240.

15. Visai et al. 2000. Monoclonal antibodies to CNA, a collagen-binding microbial surface component recognizing adhesive matrix molecules, detach *Staphylococcus aureus* from a collagen substrate. *J Biol Chem.* 275:39837–39845.

16. Rich et al. 1999. Ace is a collagen-binding MSCRAMM from *Enterococcus faecalis*. *J Biol Chem.* 274:26939–26945.

17. Maniatis et al. 1989. Molecular Cloning: A Laboratory Manual. Cold Spring Harbor Laboratory, Cold Spring Harbor, N.Y.

18. Brown et al. 2001. The effect of UV irradiation on infection of mice with *Borrelia burgdorferi*. *Photochem Photobiol.* 73:537–544.

19. Brown et al. 2001. Resistance to Lyme disease in decorin-deficient mice. *J Clin Invest.* 107:845–852.

20. Pride et al. 1998. Specific Th1 cell lines that confer protective immunity against experimental *Borrelia burgdorferi* infection in mice. *J Leukoc Biol.* 63:542–549.

21. Switalski et al. 1993. A collagen receptor on *Staphylococcus aureus* strains isolated from patients with septic arthritis mediates adhesion to cartilage. *Mol Microbiol.* 7:99–107.

22. Brown et al. 1995. Modulation of immunity to *Borrelia burgdorferi* by ultraviolet irradiation: differential effect on Th1 and Th2 immune responses. *Eur J Immunol.* 25:3017–3022.

23. Bremell et al. 1991. Experimental *Staphylococcus aureus* arthritis in mice. *Infect. Immun.* 59:2615–2623.

24. Patti et al. 1994. MSCRAMM-mediated adherence of microorganisms to host tissues. *Annu Rev Microbiol.* 48:585–617.

25. Chang et al. 2000. Use of pulsed-field gel electrophoresis in the analysis of recurrent *Staphylococcus aureus* infections in patients on continuous ambulatory peritoneal dialysis. *Am J Nephrol.* 20:463–467.

26. Hartstein et al. 1992. Recurrent *Staphylococcus aureus* bacteremia. *J Clin Microbiol.* 30:670–4.

27. Monteil et al. 1987. Selective immunodeficiency affecting staphylococcal response. *Lancet.* 2:880–883.

28. Shayegani et al. 1973. Cell-mediated immunity in mice infected with *S. aureus* and elicited with specific bacterial antigens. *J Reticuloendothel Soc.* 14:44–51.

29. Sarai et al. 1977. Immunological properties in staphylococcal toxic epidermal necrolysis. *Dermatologica.* 155:315–318.

30. Verbrugh et al. 1980. Phagocytic and chemotactic function of polymorphonuclear and mononuclear leucocytes in patients with recurrent staphylococcal infections. *Scand J Infect Dis.* 12:111–116.

31. Ficker et al. 1989. Staphylococcal infection and the limbus: study of the cell-mediated immune response. *Eye.* 3:190–193.

32. Easmon et al. 1975. Cell-mediated immune responses in *Staphylococcus aureus* infections in mice. *Immunology.* 29:75–85.

33. Valmin et al. 1982. Recurrent *Staphylococcal furunculosis:* lymphocyte subsets and plasma immunoglobulins. *Scand J Infect Dis.* 14:153–154.

34. Herman et al. 1991. Superantigens: mechanism of T-cell stimulation and role in immune responses. *Annu Rev Immunol.* 9:745–772.

35. Uhlen et al. 1984. Complete sequence of the staphylococcal gene encoding protein A. A gene evolved through multiple duplications. *J Biol Chem.* 259:1695–1702.

36. Uhlen et al. 1984. Expression of the gene encoding protein A in *Staphylococcus aureus* and coagulase-negative staphylococci. *J Bacteriol.* 159:713–719.

---

What is claimed is:

1. A method of suppressing or modulating a deleterious T cell-mediated immune response in a human or animal patient comprising administering to said patient an isolated *Staphylococcus aureus* Map protein having the amino acid sequence of SEQ ID NO: 2 in an amount effective to suppress or modulate said deleterious T cell-mediated immune response in said patient.

2. The method of claim 1, wherein the deleterious T cell-mediated immune response is delayed-type hypersensitivity (DTH).

3. A method of treating a pathological condition associated with overstimulation of T cells in a human or animal patient comprising administering to said patient an isolated *Staphylococcus aureus* Map protein having the amino acid sequence of SEQ ID NO: 2 in an amount effective to treat said condition in said patient.

4. The method of claim 3, wherein the pathological condition associated with overstimulation of T cells is staphylococcal toxic shock syndrome.

* * * * *

SEQUENCE LISTING

<160> NUMBER OF SEQ ID NOS: 4

<210> SEQ ID NO 1
<211> LENGTH: 603
<212> TYPE: DNA
<213> ORGANISM: Staphylococcus aureus
<220> FEATURE:
<221> NAME/KEY: CDS
<222> LOCATION: (1)..(603)
<223> OTHER INFORMATION:

<400> SEQUENCE: 1

```
atg aga gga tcg cat cac cat cac cat cac gga tcc cag att cca tat      48
Met Arg Gly Ser His His His His His His Gly Ser Gln Ile Pro Tyr
1               5                   10                  15 aca atc act gtg aat ggt aca agc caa aac att tta tca agc tta aca      96
Thr Ile Thr Val Asn Gly Thr Ser Gln Asn Ile Leu Ser Ser Leu Thr
                20                  25                  30 ttt aat aag aat caa caa att agt tat aaa gat ata gag aat aaa gtt     144
Phe Asn Lys Asn Gln Gln Ile Ser Tyr Lys Asp Ile Glu Asn Lys Val
            35                  40                  45 aaa tca gtt tta tac ttt aat aga ggt att agt gat atc gat tta aga     192
Lys Ser Val Leu Tyr Phe Asn Arg Gly Ile Ser Asp Ile Asp Leu Arg
50                  55                  60 ctt tct aag caa gca aaa tac acg gtt cat ttt aag aat gga aca aaa     240
Leu Ser Lys Gln Ala Lys Tyr Thr Val His Phe Lys Asn Gly Thr Lys
65                  70                  75                  80 aga gtt gtc gat ttg aaa gca ggc att cac aca gcc gac tta atc aat     288
Arg Val Val Asp Leu Lys Ala Gly Ile His Thr Ala Asp Leu Ile Asn
                85                  90                  95 aca agt gac att aaa gca att agt gtt aac gta gat act aaa aag caa     336
Thr Ser Asp Ile Lys Ala Ile Ser Val Asn Val Asp Thr Lys Lys Gln
            100                 105                 110 gtg aaa gat aaa gag gca aaa gca aat gtt caa gtg ccg tat aca atc     384
Val Lys Asp Lys Glu Ala Lys Ala Asn Val Gln Val Pro Tyr Thr Ile
        115                 120                 125 act gtg aat ggt aca agc caa aac att tta tca aac tta aca ttt aaa     432
Thr Val Asn Gly Thr Ser Gln Asn Ile Leu Ser Asn Leu Thr Phe Lys
    130                 135                 140 aag aat cag caa att agt tat aaa gat tta gag aat aat gta aaa tca     480
Lys Asn Gln Gln Ile Ser Tyr Lys Asp Leu Glu Asn Asn Val Lys Ser
145                 150                 155                 160 gtt tta aaa tca aac aga ggt ata act gat gta gat tta aga ctt tca     528
Val Leu Lys Ser Asn Arg Gly Ile Thr Asp Val Asp Leu Arg Leu Ser
                165                 170                 175 aaa caa gcg aaa ttt aca gtt aat ttt aaa aat ggc acg aaa aaa gtt     576
Lys Gln Ala Lys Phe Thr Val Asn Phe Lys Asn Gly Thr Lys Lys Val
```

```
                    180             185             190
atc gat ttg aaa gca ggc att tat tga                              603
Ile Asp Leu Lys Ala Gly Ile Tyr
        195             200

<210> SEQ ID NO 2
<211> LENGTH: 200
<212> TYPE: PRT
<213> ORGANISM: Staphylococcus aureus

<400> SEQUENCE: 2

Met Arg Gly Ser His His His His His Gly Ser Gln Ile Pro Tyr
1               5                   10                  15

Thr Ile Thr Val Asn Gly Thr Ser Gln Asn Ile Leu Ser Ser Leu Thr
            20                  25                  30

Phe Asn Lys Asn Gln Gln Ile Ser Tyr Lys Asp Ile Glu Asn Lys Val
        35                  40                  45

Lys Ser Val Leu Tyr Phe Asn Arg Gly Ile Ser Asp Ile Asp Leu Arg
    50                  55                  60

Leu Ser Lys Gln Ala Lys Tyr Thr Val His Phe Lys Asn Gly Thr Lys
65                  70                  75                  80

Arg Val Val Asp Leu Lys Ala Gly Ile His Thr Ala Asp Leu Ile Asn
                85                  90                  95

Thr Ser Asp Ile Lys Ala Ile Ser Val Asn Val Asp Thr Lys Lys Gln
            100                 105                 110

Val Lys Asp Lys Glu Ala Lys Ala Asn Val Gln Val Pro Tyr Thr Ile
        115                 120                 125

Thr Val Asn Gly Thr Ser Gln Asn Ile Leu Ser Asn Leu Thr Phe Lys
    130                 135                 140

Lys Asn Gln Gln Ile Ser Tyr Lys Asp Leu Glu Asn Asn Val Lys Ser
145                 150                 155                 160

Val Leu Lys Ser Asn Arg Gly Ile Thr Asp Val Asp Leu Arg Leu Ser
                165                 170                 175

Lys Gln Ala Lys Phe Thr Val Asn Phe Lys Asn Gly Thr Lys Lys Val
            180                 185                 190

Ile Asp Leu Lys Ala Gly Ile Tyr
        195                 200

<210> SEQ ID NO 3
<211> LENGTH: 396
<212> TYPE: DNA
<213> ORGANISM: Staphylococcus aureus
<220> FEATURE:
<221> NAME/KEY: CDS
<222> LOCATION: (1)..(396)
<223> OTHER INFORMATION:

<400> SEQUENCE: 3 atg aga gga tcg cat cac cat cac cat cac gga tcc cag att cca tat    48
Met Arg Gly Ser His His His His His Gly Ser Gln Ile Pro Tyr
1               5                   10                  15 aca atc act gtg aat ggt aca agc caa aac att tta tca agc tta aca    96
Thr Ile Thr Val Asn Gly Thr Ser Gln Asn Ile Leu Ser Ser Leu Thr
            20                  25                  30 ttt aat aag aat caa caa att agt tat aaa gat ata gag aat aaa gtt   144
Phe Asn Lys Asn Gln Gln Ile Ser Tyr Lys Asp Ile Glu Asn Lys Val
        35                  40                  45 aaa tca gtt tta tac ttt aat aga ggt att agt gat atc gat tta aga   192
Lys Ser Val Leu Tyr Phe Asn Arg Gly Ile Ser Asp Ile Asp Leu Arg
    50                  55                  60
```

-continued

```
    50                  55                  60 ctt tct aag caa gca aaa tac acg gtt cat ttt aag aat gga aca aaa      240
Leu Ser Lys Gln Ala Lys Tyr Thr Val His Phe Lys Asn Gly Thr Lys
65                  70                  75                  80 aga gtt gtc gat ttg aaa gca ggc att cac aca gcc gac tta atc aat      288
Arg Val Val Asp Leu Lys Ala Gly Ile His Thr Ala Asp Leu Ile Asn
                85                  90                  95 aca agt gac att aaa gca att agt gtt aac gta gat act aaa aag caa      336
Thr Ser Asp Ile Lys Ala Ile Ser Val Asn Val Asp Thr Lys Lys Gln
            100                 105                 110 gtg aaa gat aaa gag gca aaa gca aat gtt gtc gac ctg cag cca agc      384
Val Lys Asp Lys Glu Ala Lys Ala Asn Val Val Asp Leu Gln Pro Ser
        115                 120                 125 tta att agc tga                                                      396
Leu Ile Ser
    130

<210> SEQ ID NO 4
<211> LENGTH: 131
<212> TYPE: PRT
<213> ORGANISM: Staphylococcus aureus

<400> SEQUENCE: 4

Met Arg Gly Ser His His His His His His Gly Ser Gln Ile Pro Tyr
1               5                   10                  15

Thr Ile Thr Val Asn Gly Thr Ser Gln Asn Ile Leu Ser Ser Leu Thr
            20                  25                  30

Phe Asn Lys Asn Gln Gln Ile Ser Tyr Lys Asp Ile Glu Asn Lys Val
        35                  40                  45

Lys Ser Val Leu Tyr Phe Asn Arg Gly Ile Ser Asp Ile Asp Leu Arg
    50                  55                  60

Leu Ser Lys Gln Ala Lys Tyr Thr Val His Phe Lys Asn Gly Thr Lys
65                  70                  75                  80

Arg Val Val Asp Leu Lys Ala Gly Ile His Thr Ala Asp Leu Ile Asn
                85                  90                  95

Thr Ser Asp Ile Lys Ala Ile Ser Val Asn Val Asp Thr Lys Lys Gln
            100                 105                 110

Val Lys Asp Lys Glu Ala Lys Ala Asn Val Val Asp Leu Gln Pro Ser
        115                 120                 125

Leu Ile Ser
    130
```